US009028525B2

(12) United States Patent
Hallisey

(10) Patent No.: US 9,028,525 B2
(45) Date of Patent: *May 12, 2015

(54) PERCUTANEOUS RETRIEVABLE VASCULAR FILTER

(75) Inventor: Michael J. Hallisey, Wethersfield, CT (US)

(73) Assignee: Merit Medical Systems, Inc., South Jordan, UT (US)

( * ) Notice: Subject to any disclaimer, the term of this patent is extended or adjusted under 35 U.S.C. 154(b) by 560 days.

This patent is subject to a terminal disclaimer.

(21) Appl. No.: 13/286,653

(22) Filed: Nov. 1, 2011

(65) Prior Publication Data

US 2012/0109181 A1    May 3, 2012

Related U.S. Application Data

(63) Continuation of application No. 12/203,515, filed on Sep. 3, 2008, now Pat. No. 8,062,328.

(60) Provisional application No. 60/967,704, filed on Sep. 7, 2007.

(51) Int. Cl.
*A61M 29/00* (2006.01)
*A61F 2/01* (2006.01)

(52) U.S. Cl.
CPC ........... *A61F 2/013* (2013.01); *A61F 2002/018* (2013.01); *A61F 2/01* (2013.01); *A61F 2002/011* (2013.01); *A61F 2250/0059* (2013.01); *A61F 2002/016* (2013.01); *A61F 2230/005* (2013.01);
(Continued)

(58) Field of Classification Search
CPC ..... A61F 2/01; A61F 2/013; A61F 2002/011; A61F 2002/018; A61F 2230/0093; A61F 2230/005; A61F 2230/0078; A61F 2230/008; A61F 2250/0059; A61F 2250/006
USPC .................. 606/108, 159, 200; 604/104–107; 623/1.11
See application file for complete search history.

(56) References Cited

U.S. PATENT DOCUMENTS 4,132,650 A    1/1979   Kirsch et al.
4,494,531 A    1/1985   Gianturco
(Continued)

FOREIGN PATENT DOCUMENTS

EP    1987800      4/2008
JP    61/41444     5/1994
(Continued)

OTHER PUBLICATIONS

U.S. Appl. No. 13/402,462, filed Aug. 5, 2011, Snow.
(Continued)

*Primary Examiner* — David Eastwood
(74) *Attorney, Agent, or Firm* — Stoel Rives LLP

(57) ABSTRACT

Retrievable vena cava filters for the temporary or permanent prevention of Pulmonary embolism (PE) are disclosed. A filter in accordance with the present invention has a tube-within-tube structure with overlapping semi-spheres. The semi-spheres comprise a plurality of expandable legs. The first tube may have a first set of expandable legs and a plurality of slots allowing for deployment of a second or third set of expandable legs on the second tube. The filter of the present invention may be retrieved by a catheter and snare. The third set of expandable legs conveys the vector force from the closing of the first set to the second set to cause it to collapse.

20 Claims, 16 Drawing Sheets

(52) U.S. Cl.
CPC ... *A61F 2230/0078* (2013.01); *A61F 2230/008* (2013.01); *A61F 2230/0093* (2013.01)

(56) References Cited

U.S. PATENT DOCUMENTS

| | | | |
|---|---|---|---|
| 4,619,246 A | 10/1986 | Molgaard-Nielsen | |
| 4,781,177 A | 11/1988 | Lebigot | |
| 4,832,055 A | 5/1989 | Palestrant | |
| 4,900,312 A | 2/1990 | Nadeau | |
| 5,133,733 A | 7/1992 | Rasmussen et al. | |
| 5,234,458 A * | 8/1993 | Metais | 606/200 |
| 5,242,462 A | 9/1993 | El-Nounou et al. | |
| 5,312,479 A | 5/1994 | Weinstein et al. | |
| 5,324,304 A | 6/1994 | Rasmussen | |
| 5,370,657 A | 12/1994 | Irie | |
| 5,375,612 A | 12/1994 | Cottenceau et al. | |
| 5,437,655 A | 8/1995 | Bartholomew | |
| 5,484,474 A | 1/1996 | Weinstein et al. | |
| 5,601,568 A | 2/1997 | Chevillon et al. | |
| 5,626,605 A | 5/1997 | Irie | |
| 5,634,942 A | 6/1997 | Chevillon et al. | |
| 5,669,933 A | 9/1997 | Simon | |
| 5,709,704 A | 1/1998 | Nott et al. | |
| 5,795,322 A | 8/1998 | Boudewijn | |
| 5,810,874 A | 9/1998 | Lefebvre | |
| 5,836,968 A | 11/1998 | Simon et al. | |
| 5,836,969 A | 11/1998 | Kim | |
| 5,853,420 A | 12/1998 | Chevillon et al. | |
| 5,879,381 A | 3/1999 | Moriuchi | |
| 5,954,741 A | 9/1999 | Fox | |
| 5,976,172 A | 11/1999 | Homsma et al. | |
| 5,984,947 A | 11/1999 | Smith | |
| 6,007,558 A | 12/1999 | Ravenscroft et al. | |
| 6,013,093 A | 1/2000 | Nott et al. | |
| 6,059,825 A | 5/2000 | Hobbs | |
| 6,099,549 A | 8/2000 | Bosma et al. | |
| 6,117,165 A | 9/2000 | Becker | |
| 6,156,055 A | 12/2000 | Ravenscroft | |
| 6,193,739 B1 | 2/2001 | Chevillon et al. | |
| 6,214,025 B1 | 4/2001 | Thistle et al. | |
| 6,241,746 B1 | 6/2001 | Bosma et al. | |
| 6,258,026 B1 | 7/2001 | Ravenscroft et al. | |
| 6,267,777 B1 | 7/2001 | Bosma et al. | |
| 6,273,900 B1 | 8/2001 | Nott et al. | |
| 6,273,901 B1 | 8/2001 | Whitcher et al. | |
| 6,306,141 B1 | 10/2001 | Jervis | |
| 6,328,719 B1 | 12/2001 | Holtermann et al. | |
| 6,347,711 B1 | 2/2002 | Goebel et al. | |
| 6,391,045 B1 | 5/2002 | Kim | |
| 6,428,559 B1 | 8/2002 | Johnson | |
| 6,436,121 B1 | 8/2002 | Blom | |
| 6,443,972 B1 | 9/2002 | Bosma | |
| 6,461,370 B1 | 10/2002 | Gray et al. | |
| 6,468,290 B1 | 10/2002 | Weldon et al. | |
| 6,485,501 B1 | 11/2002 | Green | |
| 6,506,205 B2 | 1/2003 | Goldberg et al. | |
| 6,511,496 B1 | 1/2003 | Huter et al. | |
| 6,527,962 B1 | 3/2003 | Nadal | |
| 6,540,722 B1 | 4/2003 | Boyle et al. | |
| 6,540,768 B1 | 4/2003 | Diaz et al. | |
| 6,589,266 B2 | 7/2003 | Whitcher et al. | |
| 6,596,011 B2 | 7/2003 | Johnson et al. | |
| 6,620,183 B2 | 9/2003 | DiMatteo | |
| 6,623,506 B2 | 9/2003 | McGuckin, Jr. et al. | |
| 6,656,203 B2 | 12/2003 | Roth et al. | |
| 6,660,021 B1 | 12/2003 | Palmer et al. | |
| 6,726,701 B2 | 4/2004 | Gilson | |
| 6,783,538 B2 | 8/2004 | McGuckin, Jr. et al. | |
| 6,793,665 B2 | 9/2004 | McGuckin, Jr. et al. | |
| 6,932,831 B2 | 8/2005 | Forber | |
| 6,939,361 B1 | 9/2005 | Kleshinski | |
| 6,958,074 B2 | 10/2005 | Russell | |
| 6,989,021 B2 | 1/2006 | Bosma | |
| 6,991,641 B2 | 1/2006 | Diaz et al. | |
| 7,147,649 B2 | 12/2006 | Thomas | |
| 7,179,275 B2 * | 2/2007 | McGuckin et al. | 606/200 |
| 7,261,731 B2 | 8/2007 | Patel | |
| 7,279,000 B2 | 10/2007 | Cartier et al. | |
| 7,314,477 B1 | 1/2008 | Ravenscroft et al. | |
| 7,323,002 B2 | 1/2008 | Johnson et al. | |
| 7,329,227 B2 | 2/2008 | Schramm | |
| 7,329,269 B2 | 2/2008 | Shapiro et al. | |
| 7,338,512 B2 | 3/2008 | McGuckin, Jr. et al. | |
| 7,344,549 B2 | 3/2008 | Boyle et al. | |
| 7,399,308 B2 | 7/2008 | Borillo et al. | |
| 7,534,251 B2 | 5/2009 | WasDyke | |
| 7,544,202 B2 | 6/2009 | Cartier et al. | |
| 7,582,100 B2 | 9/2009 | Johnson | |
| 7,625,390 B2 | 12/2009 | Hendriksen et al. | |
| 7,699,865 B2 | 4/2010 | Johnson et al. | |
| 7,699,867 B2 | 4/2010 | Hendriksen et al. | |
| 7,704,266 B2 | 4/2010 | Thinnes, Jr. et al. | |
| 7,704,267 B2 | 4/2010 | Tessmer | |
| 7,736,383 B2 | 6/2010 | Bressler et al. | |
| 7,749,246 B2 | 7/2010 | McGuckin et al. | |
| 7,763,045 B2 | 7/2010 | Osborne | |
| 7,771,452 B2 | 8/2010 | Pal et al. | |
| 7,780,694 B2 | 8/2010 | Palmer et al. | |
| 7,794,473 B2 | 9/2010 | Tessmer et al. | |
| 7,803,171 B1 | 9/2010 | Uflacker | |
| 7,862,577 B2 | 1/2011 | Gray et al. | |
| 7,887,561 B2 | 2/2011 | McGuckin, Jr. et al. | |
| 7,909,847 B2 | 3/2011 | McGuckin, Jr. et al. | |
| 7,931,664 B2 | 4/2011 | Gray et al. | |
| 7,959,647 B2 | 6/2011 | Palmer | |
| 7,967,838 B2 | 6/2011 | Chanduszko et al. | |
| 7,972,353 B2 | 7/2011 | Hendriksen et al. | |
| 7,976,562 B2 | 7/2011 | Bressler et al. | |
| 7,996,993 B2 | 8/2011 | Gray et al. | |
| 8,025,675 B2 | 9/2011 | Shirley et al. | |
| 8,029,529 B1 | 10/2011 | Chankduszko | |
| 8,043,322 B2 | 10/2011 | Hendriksen et al. | |
| 8,057,506 B2 * | 11/2011 | Gilson et al. | 606/200 |
| 8,057,507 B2 | 11/2011 | Horan et al. | |
| 8,062,326 B2 | 11/2011 | McGuckin, Jr. et al. | |
| 8,062,327 B2 | 11/2011 | Chanduszko et al. | |
| 8,062,328 B2 * | 11/2011 | Hallisey | 606/200 |
| 8,092,484 B2 | 1/2012 | Kashkarov et al. | |
| 8,092,485 B2 | 1/2012 | Lapid | |
| 8,100,936 B2 | 1/2012 | McGuckin, Jr. et al. | |
| 8,105,349 B2 | 1/2012 | Hendriksen et al. | |
| 8,118,828 B2 | 2/2012 | Cartier et al. | |
| 8,133,251 B2 | 3/2012 | Ravenscroft et al. | |
| 8,133,252 B2 | 3/2012 | Davis et al. | |
| 8,162,972 B2 | 4/2012 | McGuckin, Jr. et al. | |
| 8,167,901 B2 | 5/2012 | Hendriksen et al. | |
| 8,211,140 B2 | 7/2012 | McGunkin, Jr. et al. | |
| 8,246,648 B2 | 8/2012 | Tekulve | |
| 8,246,650 B2 | 8/2012 | Osborne | |
| 8,246,651 B2 | 8/2012 | Hendriksen et al. | |
| 8,252,017 B2 | 8/2012 | Paul, Jr. et al. | |
| 8,252,019 B2 | 8/2012 | Fleming, III | |
| 8,267,954 B2 | 9/2012 | Decant, Jr. et al. | |
| 8,282,668 B2 | 10/2012 | McGuckin, Jr. et al. | |
| 8,317,818 B2 | 11/2012 | Kashkarov et al. | |
| 8,333,785 B2 | 12/2012 | Chanduszko et al. | |
| 8,353,926 B2 | 1/2013 | Silver | |
| 8,366,736 B2 | 2/2013 | Thinnes, Jr. et al. | |
| 8,383,926 B2 | 2/2013 | Plissonnier et al. | |
| 8,430,903 B2 | 4/2013 | Chanduszko et al. | |
| 8,475,488 B2 * | 7/2013 | Cartier et al. | 606/200 |
| 2001/0000799 A1 | 5/2001 | Wessman et al. | |
| 2001/0039432 A1 | 11/2001 | Whitcher et al. | |
| 2002/0058911 A1 * | 5/2002 | Gilson et al. | 604/96.01 |
| 2002/0062134 A1 | 5/2002 | Barbut et al. | |
| 2002/0111647 A1 | 8/2002 | Khairkhahan et al. | |
| 2003/0109897 A1 | 6/2003 | Walak et al. | |
| 2004/0087999 A1 | 5/2004 | Bosma et al. | |
| 2004/0116959 A1 | 6/2004 | McGuckin | |
| 2004/0220610 A1 | 11/2004 | Kriedler et al. | |
| 2005/0004596 A1 | 1/2005 | McGuckin, Jr. et al. | |
| 2005/0015111 A1 * | 1/2005 | McGuckin et al. | 606/200 |
| 2005/0080447 A1 | 4/2005 | McGuckin, Jr. et al. | |
| 2005/0222604 A1 | 10/2005 | Shaeffer | |

(56) References Cited

U.S. PATENT DOCUMENTS

| | | | |
|---|---|---|---|
| 2005/0267515 A1 | 12/2005 | Oliva et al. | |
| 2005/0288704 A1* | 12/2005 | Cartier et al. | 606/200 |
| 2005/0288705 A1 | 12/2005 | Gilson | |
| 2006/0009799 A1 | 1/2006 | Kleshinski et al. | |
| 2006/0041271 A1 | 2/2006 | Bosma et al. | |
| 2006/0079928 A1 | 4/2006 | Cartier | |
| 2006/0079930 A1 | 4/2006 | McGuckin et al. | |
| 2006/0100659 A1 | 5/2006 | Dinh et al. | |
| 2006/0106417 A1 | 5/2006 | Tessmer | |
| 2006/0206138 A1 | 9/2006 | Eidenschink | |
| 2007/0005095 A1 | 1/2007 | Osborne | |
| 2007/0141107 A1 | 6/2007 | Kutryk | |
| 2007/0162048 A1 | 7/2007 | Quinn et al. | |
| 2007/0167974 A1* | 7/2007 | Cully et al. | 606/200 |
| 2007/0173885 A1 | 7/2007 | Cartier | |
| 2007/0191932 A1 | 8/2007 | Kutryk | |
| 2007/0198050 A1* | 8/2007 | Ravenscroft et al. | 606/200 |
| 2008/0027481 A1 | 1/2008 | Gilson | |
| 2008/0033479 A1 | 2/2008 | Silver | |
| 2008/0097518 A1 | 4/2008 | Thinnes | |
| 2008/0234722 A1 | 9/2008 | Bonnette et al. | |
| 2008/0275487 A1 | 11/2008 | Fleming | |
| 2008/0275492 A1 | 11/2008 | Farmiga | |
| 2009/0043332 A1 | 2/2009 | Sullivan et al. | |
| 2009/0069840 A1 | 3/2009 | Hallisey | |
| 2009/0198270 A1 | 8/2009 | McGuckin, Jr. et al. | |
| 2009/0254117 A1 | 10/2009 | Pakter | |
| 2009/0299403 A1 | 12/2009 | Chanduszko et al. | |
| 2009/0299404 A1 | 12/2009 | Chanduszko et al. | |
| 2009/0306703 A1 | 12/2009 | Kashkarov et al. | |
| 2010/0049238 A1 | 2/2010 | Simpson | |
| 2010/0174310 A1 | 7/2010 | Tessmer | |
| 2010/0185229 A1 | 7/2010 | Horan et al. | |
| 2010/0185230 A1 | 7/2010 | Horan et al. | |
| 2010/0198252 A1 | 8/2010 | Beyer et al. | |
| 2010/0318115 A1 | 12/2010 | Chanduszko et al. | |
| 2011/0040321 A1 | 2/2011 | Cartier | |
| 2011/0106133 A1 | 5/2011 | O'Connell et al. | |
| 2011/0137335 A1 | 6/2011 | Hallisey | |
| 2011/0166593 A1 | 7/2011 | Paul, Jr. | |
| 2011/0202086 A1 | 8/2011 | Bates | |
| 2011/0208233 A1 | 8/2011 | McGuckin, Jr. et al. | |
| 2012/0089173 A1 | 4/2012 | Tekulve | |
| 2012/0130418 A1 | 5/2012 | Jenson et al. | |
| 2012/0184985 A1 | 7/2012 | Ravenscroft et al. | |
| 2012/0245622 A1 | 9/2012 | McGuckin, Jr. et al. | |
| 2013/0018387 A1 | 1/2013 | Diamant | |

FOREIGN PATENT DOCUMENTS

| | | |
|---|---|---|
| JP | 2008/154276 | 7/2008 |
| WO | WO01/10342 | 2/2001 |
| WO | WO02/071977 | 9/2002 |
| WO | WO2007/084431 | 7/2007 |
| WO | WO2008/127328 | 10/2008 |
| WO | WO2009/032834 | 3/2009 |
| WO | WO2010091118 | 8/2010 |

OTHER PUBLICATIONS

U.S. Appl. No. 13/402,492, filed Aug. 5, 2011, Snow.
Office Action dated Sep. 26, 2012 for U.S. Appl. No. 12/722,484.
International Search and Written Opinion dated Jun. 13, 2013 for PCT/US2013/027427.
Office Action dated Oct. 3, 2013 for U.S. Appl. No. 12/722,484.
Office Action dated Oct. 17, 2013 for U.S. Appl. No. 13/204,492.
International Search Report and Written Opinion dated Jan. 30, 2013 for PCT/US2012/047004.
International Search Report and Written Opinion dated Jan. 30, 2013 for PCT/US2012/047023.
Notice of Allowance dated Feb. 14, 2014 for U.S. Appl. No. 13/204,492.
Notice of Allowance dated Feb. 12, 2014 for U.S. Appl. No. 13/204,462.
U.S. Appl. No. 13/774,598, filed Feb. 22, 2013, Snow.
Office Action dated Mar. 29, 2013 for U.S. Appl. No. 13/204,462.
Office Action dated Mar. 29, 2013 for U.S. Appl. No. 13/204,492.
Boothroyd et al., 'Product Design for Manufacture and Assembly.' 1994, p. 64.
International Preliminary Report for Application No. PCT/US08/75102 dated Mar. 9, 2010.
International Publication and Written Opinion for Application No. PCT/US08/75102 dated Mar. 12, 2009.
Cipolla et al., 'Complications of Vena Cava Filters: A Comprehensive Clinical Review.' OPUS 12 Scientist 2008; vol. 2, No. 2: 11-24.
Katsamouris et al. 'Inferior Vena Cava Filters: In Vitro Comparison of Clot Trapping and Flow Dynamics.' Radiology 1988; 166:361-366.
Prince et al., 'The diameter of the inferior Vena Cava and It's Implications for the Use of Vena Caval Filters.' Radiology 1983; 149:687-689.
Simon et al., 'Comparative Evaluation of Clinically Available Inferior Vena Cava Filters with an In Vitro Physiologic Simulation of the Vena Cava.' Radiology 1993; 189:769-774.
Lorch et al., 'In Vitro Studies of Temporary Vena Cava Filters.' CardioVascular and Interventional Radiology 1998; 21:146-150.
Neuerburg et al., 'New Retrievable Percutaneous Vena Cava Filter: Experimental In Vitro and In Vivo Evaluation.' CardioVascular and Interventional Radiology 1993: 16:224-229.
Reekers et al., 'Evaluation of the Retrievability of the OptEase IVC Filter in an Animal Model.' J Vasc Intery Radiol 2004; 15:261-267.
Kinney, 'Update on Inferior Vena Cava Filters.' J Vasc Interv Radiol 2003; 14:425-440.
Bruckheimer et al., 'In Vitro Evaluation of a Retrievable Low-Profile Nitinol Vena Cava Filter.' J Vasc Interv Radiol 2003; 14:469-474.
Brountzos et al., 'A New Optional Vena Cava Filter: Retrieval at 12 Weeks in an Animal Model.' J Vasc Interv Radiol 2003; 14:763-772.
Ray et al., 'Outcomes with Retrievable Inferior Vena Cava Filters: A Multicenter Study.' J Vasc Interv Radiol 2006; 17:1595-1604.
Kaufman et al., 'Guidelines for the Use of Retrievable and Convertible Vena Cava Filters: Report from the Society of Interventional Radiology Mulitdisciplinary consensus conference.' J Vasc Interv Radiol 2006; 17:449-459.
Kolbeck et al., 'Optional Inferior Vena Cava Filter Retrieval with Retained Thrombus: An In Vitro Model.' J Vasc Interv Radiol 2006; 17:685-691.
Lorch et al., 'Current Practice of Temporary Vena Cava Filter Insertion: A Multicenter Registry.' JVIR 2000; 11:83-88.
Rousseau et al., 'The 6-F Nitinol TrapEase Inferior Vena Cava Filter: Results of a Prospective Multicenter Trial.' J Vasc Interv Radiol 2001; 12:299-304.
Stoneham et al., 'Temporary Inferior Vena Cava Filters: In Vitro Comparison with Permanent IVC Filters.' JVIR 1995; 6:731-736.
Crochet et al., 'Evaluation of the LGM Vena Cava-Tech Infrarenal Vena Cava Filter in and Ovine Venous Thromboembolism Model.' J Vasc Interv Radiol 2001; 12:739-745.
Kaufman, 'Guidelines for the Use of Optional Retrievable Vena Cava Filters.' European Respiratory Disease 2007; 31-34.
Epstein et al., 'Experience with the Amplatz Retrievable Vena Cava Filter.' Radiology 1989; 172:105-110.
Inferior Vena Cava Filter, ISI Interventional & Surgical Innovations LLC. Product Brochure, Copyright 2008.
The Clot Stopper (online) Retrieved from the internet URL:http://www.americanheritage.com/people/articles/web/20060715-pulmonary-embolism-blood-clot-lazar-greenfield-garman-kimmel-surgery-medical-doctor-surgeon.shtml Summer 2006, vol. 22 Issue 1.
Simon Nitinol Filter, Versatile and Dependable Performance. Bard Peripheral Vascular (online) Retrieved from the internet URL:http://www.bardpv.com_vascular/product.php?p=23 Copyright 2004.
Aegisy Vena Cava Filter. Shenzhen Lifetech Scientific Inc. (online). Retrieved from the internet URL:http://www.lifetechmed.com/english/product/product6.htm Copyright 2005.
Safe Flo Vena Cava Filter (online) Retrieved from the internet <URL:www.rafaelmedical.com>.
Aegisy Vena Cava Filter Product Description (online) Retrieved from the internet URL:http://www.lifetechclinic.com/upload/article/vena/instruction_for_use.htm Accessed Jun. 6, 2008.

(56) References Cited

OTHER PUBLICATIONS

Design History (online). Retrieved from the internet URL:http://www.lifetechclinic.com/upload/vena/vena_cava_filter.htm Accessed Jun. 6, 2008.

Crux Biomedical, Inc. Inferior Vena Cava Filter System Instructions for Use, IFU P/N 0001 Rev.B, DCO# 0027, Effective Date Feb. 2, 2007.

Smouse, 'Next Generation Filters: Are There Improvements Over the Existing Filters?', Powerpoint Presentation. University of Illinois College of Medicine at Peoria.

Kaufman, 'Vena Cava Filters as a Risk Factor for VTE'. Powerpoint Presentation at the SIR Foundation Jun. 2007 IVC Filter Research Consensus Panel.

Rectenwald, 'Are All IVC's the Same.' Powerpoint Presentation at the SIR Foundation Jun. 2007 IVC Filter Research Consensus Panel.

Rogers, 'Vena Cava Filter Outcomes.' Powerpoint Presentation at the SIR Foundation Jun. 2007 IVC Filter Research Consensus Panel.

SIR Foundation Research Consensus Panel for the Development of a Research Agenda in Inferior Vena Cava Filters, Jun. 12, 2007—Herndon, VA. Powerpoint Presentation at the SIR Foundation Jun. 2007 IVC Filter Research Consensus Panel.

TrapEase Vena Cava Filter User's Instruction. Cordis Corp. No date available.

Corriere et al., 'Vena Cava Filters: An Update.' Future Cardiol 2006: 2(6): 695-707.

Mohan, C. et al. 'Comparative Efficacy and Complications of Vena Caval Filters.' J Vasc Surg 1995; 21:235-246.

Linsenmaier, U. et al., 'Indications, Management, and Complications of Temporary Inferior Vena Cava Filters.' Cardiovascular Intervent, Radiol 1998; 21(6): 464-469.

Asch et al. Radiology 2002; 29:173-176.

Cunliffe et al., 'A Fatal Complication of a Vena Cava Filter Associated with Pulmonary Thromboembolism.' Am J Forensic Med Pathol 2008; 29:173-176.

Joels et al., 'Complications of Inferior Vena Cava Filters.' Am Surg 2003; 69:654-659.

Pulmonary Embolism (online). Retrieved from internet URL:http//www.mayoclinic.com/health/pulmonary-embolism/DS00429/DSECTION=complications By Mayo Clinic Staff Sep. 28, 2007.

Cordis TrapEase Permanent Vena Cava Filter with the VisEase Angiographic Vessel Dilator (on line). Retrieved from <URL:http//www.mitek.com/home.jhtml?loc=USENG&page=viewcontent&contentid=09008b9880ffdcbf&nodekey=1Prod_Info/Type/Endovascular_Disease_Management/Vena_Cava_Filters&parentid=fc0de00100001215> 2000-2008.

Decousus et al., 'A Clinical Trial of Vena Caval Filters in the Prevention of Pulmonary Embolism in Patients with Proximal Deep-Vein Thrombosis.' The New England Journal of Medicine, Feb. 12, 1998; vol. 338, No. 7.

Notice of Allowance for U.S. Appl. No. 12/203,515 dated Jul. 13, 2011.

Restriction Requirement dated Nov. 21, 2011 for U.S. Appl. No. 12/722,484.

Office Action dated Mar. 6, 2012 for U.S. Appl. No. 12/722,484.

Notice of Allowance dated Apr. 16, 2014 for U.S. Appl. No. 12/722,484.

International Search Report and Written Opinion dated Nov. 13, 2014 for PCT/US2014/050176.

Extended European Search Report dated Nov. 20, 2014 for EP12821778.3.

Extended European Search Report dated Nov. 20, 2014 for EP12822068.8.

* cited by examiner (a)          (b)          (c)

(d)          (e)          (f)

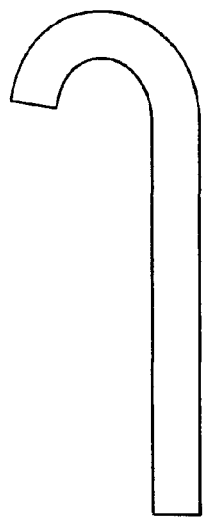 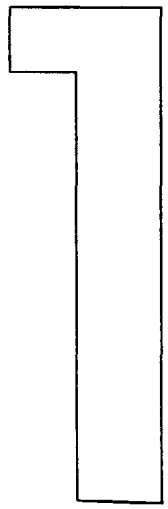 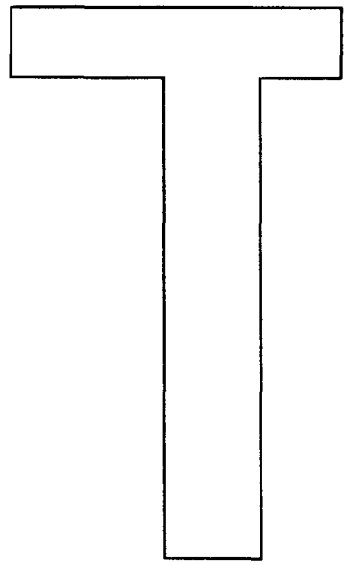
FIG. 10A    FIG. 10B    FIG. 10C
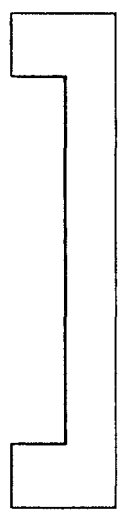 
FIG. 10D    FIG. 10E

PERCUTANEOUS RETRIEVABLE VASCULAR FILTER

RELATED APPLICATIONS

This patent application is a continuation of U.S. patent application Ser. No. 12/203,515, entitled PERCUTANEOUS PERMANENT RETRIEVABLE VASCULAR FILTER, filed on Sep. 3, 2008 now U.S. Pat No. 8,062,328 which claims the benefit under 35 U.S.C. §119(e) of U.S. Provisional Application No. 60/967,704, filed on Sep. 7, 2007, both disclosures of which are herein incorporated by reference in their entirety.

FIELD OF THE INVENTION

The present invention relates to filters within a vessel. In particular, the present invention relates to retrievable vena cava filters which may be permanent or retrievable.

BACKGROUND OF THE INVENTION

Pulmonary embolism (PE) is a common health problem and a leading cause of death in all age groups. Most pulmonary emboli result from deep vein thrombosis (DVT) in the lower extremities or pelvis. The blood clots that form in another part of the body can migrate through the veins back to the heart and into the lungs, leading to a pulmonary infarct by depriving the blood and oxygen supply to a portion of the lung. An important risk factor for the development of DVT is venostasis; common scenarios include bedridden trauma patients and passengers on long airplane flights. Other causes of DVT are hypercoagulability and vessel wall inflammation. Corriere M, et al. Vena cava filters: an update. Future Cardiol. 2(6): 695-707 (2006).

Untreated PE is associated with a high mortality rate, generally held to be about 30%, with 11% of patients dying within the first hour. Patients with recurrent PE are at much higher risk. However, when the condition is promptly treated, the survival rate increases significantly. Pulmonary embolism [on-line]. Retrieved on Jul. 11, 2008 from http://www.mayoclinic.com/health/pulmonary-embolism/DS00429/DSECTION=complications. Anticoagulant therapy, such as heparin and warfarin, is the first line of treatment for PE. For patients in whom anticoagulation is contraindicated or inadequate, such as trauma and cancer patients, vena cava filters, including inferior vena cava (IVC) filters, provide alternative protection from PE. Corriere M, et al. Vena cava filters: an update. Future Cardiol. 2(6): 695-707 (2006). Vena cava filters are typically metal devices deployed under fluoroscopic guidance into the vena cava to prevent blood clots from migrating to the lungs. An IVC filter is usually placed below the level of the renal veins with the tip above the outflow of the renal veins. When the blood clot is captured in the top of the filter, it is then washed and lysed by the influx of the blood flow.

While some vena cava filters are permanently placed in the patient, there are potential complications associated with long-term filter implantation, including thrombotic occlusion of the vena cava, filter migration, filter fragmentation and filter embolization. Mohan C, et al. Comparative efficacy and complications of vena caval filters. J. Vasc. Surg. 21:235-246 (1995). See also U.S. Pat. No. 7,261,731. Nonpermanent filters, including temporary and retrievable filters, are recommended for patients having a limited period of risk for PE or the contraindication to anticoagulation. These types of filters are also recommended in adolescent and young-adult patients with normal life expectancy. Linsenmaier U et al. Indications, management, and complications of temporary inferior vena cava filters. Cardiovasc. Intervent. Radiol. 21(6): 464-469 (1998). Some temporary vena cava filters are attached to a wire or catheter, which is either exteriorized or secured subcutaneously for filter removal. The peripheral tether causes a certain degree of patient immobility and increases the risk of infection. Murray A, et al. Radiology 225:835-844 (2002).

In U.S. Pat. No. 6,391,045, a vena cava filter is disclosed that comprises a set of helical filter-wires joined at a central region and terminating in free ends constructed to engage the vessel wall. A major mid-portion of the length of the free-ended wires are generally helical forming shape. Anchoring is accomplished by a separate assembly formed of struts and anchoring devices. A trapezoid supporting strut assembly and other means for providing linear engagement with the wall of the vena cava are also disclosed. U.S. Pat. No. 6,059,825 discloses a retrievable vena cava filter formed of a single high-memory wire. The wire has a coiled cylindrical portion and a coiled conical portion. The coils of the cylindrical portion have a sufficiently large diameter contact the walls of the inferior vena cava with sufficient force to hold the coils in place against the inferior vena cava. The conical portion of the wire has a segment that aids in the removing of the filter from the vena. The vena cava filter of U.S. Pat. No. 5,954,741 features an inflatable balloon at or near the distal end of an elongate flexible multiple-lumen core or stem. The balloon is deflated prior to insertion; it is inflated to become a filter when properly positioned in the vein, and finally it is deflated for removal purposes.

In the U.S.A., there are currently six FDA-approved permanent vena cava filters with different shapes, configurations, sizes and materials. They include the stainless steel Greenfield filter (Boston Scientific, Natick, Mass.), the Bird's Nest filter (Cook, Bloomington, Ind.), the Simon Nitinol Filter (Bard, Tempe, Ariz.), the TrapEase filter (Cordis, Miami Lakes, Fla.), the Vena-Tech filter (B. Braun Medical, Evanston, Ill.) and the G2 filter (Bard, Tempe, Ariz.). There are only two FDA-approved retrievable vena cava filters: the Gunter-Tulip filter (Cook, Bloomington, Ind.) and the OptEase filter (Cordis, Miami Lakes, Fla.). Corriere M, et al. Vena cava filters: an update. Future Cardiol. 2(6): 695-707 (2006).

Retrievable vena cava filters are designed with specific features, so depending on the individual situation, they may either be left in the vessel permanently or be retrieved. While the versatility of retrievable filters makes them favorable options, in clinical practice, a large number of the retrievable filters are prone to migration and tilt. Filters have been reported to migrate to the heart, pulmonary vasculature, and distally, along with subsequent vascular perforation due to filter strut extrusion. Cunliffe C, et al. A fatal complication of a vena cava filter associated with pulmonary thromboembolism. Am. J. Forensic. Med. Pathol. 29: 173-176 (2008). Filter tilt seriously reduces the filtering efficiency. The tilt of greater than 14 degrees from the longitudinal axis is considered to be associated with the increased incidence of recurrent PE. Joels C, et al. Complications of inferior vena cava filters. Am Surg. 69:654-659 (2003). The migration or tilt further makes it difficult or impossible to retrieve the filter.

It is, therefore, desired to develop a retrievable vena cava filter that has high filtering capacity with no impedance to flow, is securely fixed on the vena cava wall (non-migrating and non-tilting), and can be easily retrieved. It is also advantageous to develop a retrievable filter than can be deployed at the patient's bedside without the need of fluoroscopy.

SUMMARY OF THE INVENTION

It is an object of the present invention to provide a filter comprising a first tube having a plurality of a first set of expandable legs, a second tube having a plurality of a second set of expandable legs and a plurality of a third set of expandable legs. Each leg of the first set has an end secured to the first tube and a free end. Each leg of the second set has an end secured to the second tube and a free end. Each leg of the third set comprises an expandable segment and has an end secured to a third tube. The second tube's external diameter and the third tube's external diameter are less than the first tube's internal diameter. The first tube has a plurality of slots, each slot being positioned at a radial position on the first tube allowing for deployment of the expandable segment in each leg of the third set and for deployment of each expandable leg of the second set, the slots being oriented parallel to the cylindrical axis of the first tube. The second and third tubes are inserted into the first tube such that the free end of each leg in the first set is oriented in a direction opposite to the free end of each leg in the second set. The filter may be encased in a catheter in an undeployed state. Each expandable leg of the first and second sets may be deployed, and a cage may be formed comprising expandable legs from the first and second sets. The cage may form a sphere shape when the expandable legs of the first and second set are deployed. The expandable segment of each expandable leg in the third set may form a curvilinear shape when deployed. A segment of each expandable leg of the third set may be secured to a pin which lies within the second tube. Each expandable leg of the first set may have at least one barb on the free end. When the filter is deployed, the barb on the end of free end may be inserted into a vessel wall. In one embodiment, each expandable leg of the first set has one barb on the free end. An end of the first tube lying opposite to where the second and third tubes are inserted into the first tube may have at least one notch. In one embodiment, an end of the first tube lying opposite to where the second and third tubes are inserted into the first tube has one notch. Each of the expandable legs of the first and second sets may comprise memory metal. The expandable segment of the expandable legs of third set may comprise memory metal.

The number of expandable legs in the first set may range from about 2 to about 20, from about 4 to about 15, and from about 5 to about 10. In one embodiment, the number of expandable legs in the first set is five, A, B, C, D and E, the number of legs in the second set is five, F, G, H, I and J and the number of legs in the third set is five, K, L, M, N and o. The expandable legs in the first set are secured at radial positions along the first tube's circumference ranging from about 0° to about 72° for A, about 72° to about 144° for B, about 144° to about 216° for C, about 216° to about 288° for D and about 288° to about 360° for E. The radial positions of the first set of expandable legs, A, B, C, D and E may be symmetrical. In another embodiment, the expandable legs in the second set are secured at radial positions along the second tube's circumference of about 0° to about 72° for F, about 72° to about 144° for G, about 144° to about 216° for H, about 216° to about 288° for 1 and about 288° to about 360° for J where the radial positions of the second set of expandable legs, F, G, H, I and J do not correspond to the radial positions of the first set of expandable legs, A, B, C, D and E. The radial positions of the second set of expandable legs, F, G, H, I and J may be symmetrical.

The present invention further provides a method for retrieving the filter comprising inserting a catheter into a vessel where the filter is positioned on the vessel wall, pushing a snare through the catheter until the snare grabs the notch, pulling back on the snare to exert tension on the filter, pushing the catheter over the snare and each expandable leg of the first set until each expandable leg retracts from the vessel wall, each expandable leg of the third set straightens and each expandable leg of the second set retracts from vessel wall, encompassing the expandable legs of the first, second and third sets in the catheter and withdrawing the filter.

BRIEF DESCRIPTION OF THE DRAWINGS

FIG. 10 shows the configuration of various forms of the notch.

DETAILED DESCRIPTION OF THE DRAWINGS

Figure 1A:
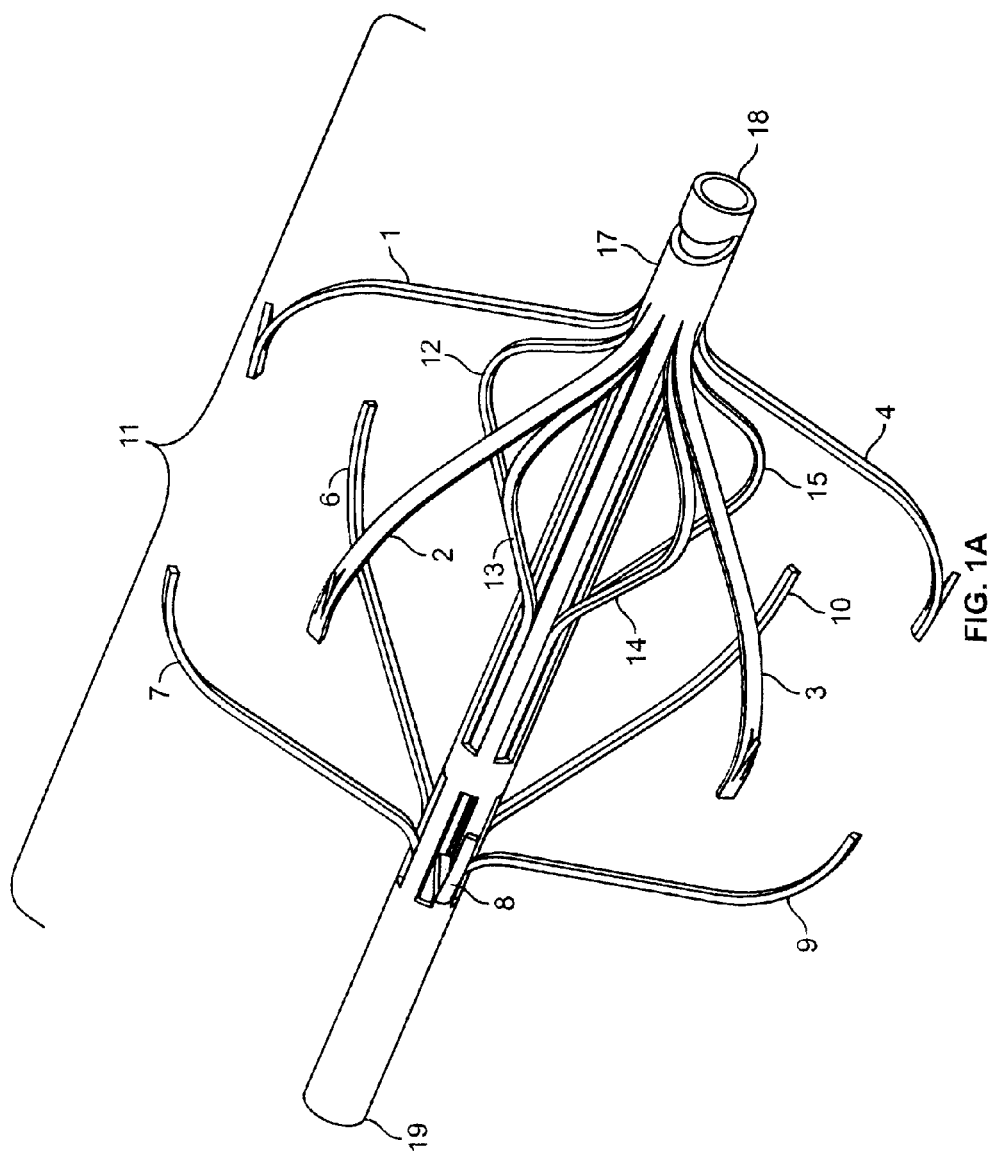
FIG. 1a shows a side view of one embodiment of the filter.

The present invention provides a vena cava filter (the "filter") that may be permanent or retrievable and which may be used for the temporary or permanent prevention of pulmonary embolism (PE). The filter can be inserted into the body percutaneously through a vein such as the femoral vein. The filter has a tube-within-tube structure that can yield semispheres which may overlap upon deployment. Together the semispheres form a cage upon deployment. The filter is positioned within the vena cava at the juncture of the renal vein. The overlapping semi-spheres or cages of the filter ensure stable and non-migrating vena cava filtration. Because the semi-spheres are collapsible, the filter can easily be retrieved from the vena cava.

The filter is formed from a first tube, second tube and a third tube which may form part of the second tube. The first tube having a plurality of a first set of expandable legs, each leg of the first set having an end secured to the first tube and a free end. The second tube has a plurality of a second set of expandable legs and a plurality of a third set of expandable legs, each leg of the second set having an end secured to the second tube and a free end, each leg of the third set comprising an expandable segment and having an end secured to a third tube which may form part of the second tube. The second tube's external diameter and the third tube's external diameter are less than the first tube's internal diameter allowing the second tube to be inserted into the first tube. The third tube and the second tube comprising a plurality of a second and a third set of expandable legs may be formed from a single piece of material or from several interconnected pieces of material. The first tube has a plurality of slots, each slot being positioned at different radial positions around the circumference of the first tube allowing for deployment of the expandable segment in each leg of the third set and for deployment of each leg of the second set, the slots being oriented parallel to the cylindrical axis of the first tube. There are at least two sets of slots, one set for the second set of expandable legs and the second set of slots for the third set of expandable legs. The radial positions of the set of slots for the second set of expandable legs may be off-set from the radial position of the slots for the third set of expandable legs.

The filter is formed by inserting the second and third tubes into the first tube such that the free end of each leg in the first set is oriented in a direction opposite to the free end of each leg in the second set forming a cage comprising legs from the first and second sets. Prior to insertion into the vena cava the filter is encased in a catheter. The free ends of the each expandable leg may have at least one barb. The number of the first, second or third set of legs of may be three, four, five or any other number that is able to ensure the stability of the filter when deployed and the efficient vena cava filtration. The legs may have various shapes, including rectangular strips, wires, tubes, rods, threads, or any other desired structure. The legs may be straight, curved, tapered or have multiple angles. The shapes, configurations or dimensions of various portions of each leg may vary or be the same. The shapes, configurations, dimensions or angles of different legs of the filter may be different or the same. The legs may be notched, barbed, hooked or in any structure that anchors the legs in the vessel wall without interfering with the retrieval of the filter.

In one embodiment, the number of legs in the first set of expandable legs is five, A, B, C, D and E, the number of legs in the second set of expandable legs is five, F, G, H, I and J and the number of legs in the third set of expandable legs is five, K, L, M, N and o. The legs in the first set are secured at radial positions along the first tube's circumference of from about 0° to about 72° for A, from about 72° to about 144° for B, from about 144° to about 216° for C, from about 216° to about 288° for D and from about 288° to about 360° for E. In one embodiment, the radial positions of the first set of expandable legs are symmetrical, e.g., A is 0°, B is at 72°, C is at 144°, D is at 216°, E is 288°. The radial positions of the first set of expandable legs may be asymmetrical.

In a further embodiment, the legs in the second set are secured at radial positions along the second tube's circumference of from about 0° to about 72° for F, from about 72° to about 144° for G, from about 144° to about 216° for H, from about 216° to about 288° for 1 and from about 288° to about 360° for J, where, in one embodiment, the radial positions of the second set, F, G, H, I and J differ from the radial positions of the first set of expandable legs, A, B, C, D, E. The radial positions of the second set of expandable legs may differ from the first set of expandable legs symmetrically or asymmetrically.

In yet a third embodiment, the legs in the third set are secured at radial positions along the second and third tube's circumference of from about 0° to about 72° for K, from about 72° to about 144° for L, from about 144° to about 216° for M, from about 216° to about 288° for N and from about 288° to about 360° for 0, where, in one embodiment, the radial positions of the third set of expandable legs, K, L, M, N and o are the same as the radial positions of second set of expandable legs. The radial positions of the third set of expandable legs may be symmetrical or asymmetrical with respect to one another.

The radial position of the second set of expandable legs may be off-set from the radial position of the first set of expandable legs. For example, if the legs in the first set are secured at radial positions along the first tube's circumference at about 72° for A, at about 144° for B, at about 216° for C, at about 288° for D and at about 360° for E, then the legs in the second set may be secured at a point half-way along the circumference between where the two first expandable legs are secured, or at about 108° for F, about 180° for G, about 252° for H, about 324° for 1 and about 360° for J. The radial position of the third set of expandable legs may be the same as the first set of expandable legs or may be off-set. For example, if the third set of expandable legs is off-set by 10° from the second set of expandable legs, then the third set of expandable legs is positioned at about 118° for K, about 190° for L, about 262° for M, about 334° for N and about 10° for O. The radial positions of the third set of expandable legs may be off-set from the second set of expandable legs by about 5° to about 50°, by about 10° to about 35° or by about 15° to about 20°.

The number of expandable legs in each set may range from 2-20, from 4-15 and from 5-10 with 5 being a preferred embodiment. There may be an equal or unequal number of legs in each of the first, second and third sets. The legs may be positioned symmetrically or asymmetrically at radial positions along the circumference of the tube. If the legs are positioned symmetrically, then the radial distance between each pair of legs, e.g., A-B and B-C is equal. The radial positions listed for the legs here are only provided for illustration purposes and the legs may be positioned by one of ordinary skill in the art without undue experimentation at any point along the circumference of the tube. For example, if there are 8 legs in the first expandable set, the positioning of the legs may be determined by dividing 360° by N where N is the number of legs. Where N=8, the legs may be positioned symmetrically at 45° intervals around the circumference of the tube. The second set of expandable legs may then positioned at off-set intervals on the circumference different from the 45° intervals, i.e., 0° (360°). 45°, 90°, 135°, 180°, 225°, 270°, 315°. The third set of expandable legs can then be positioned at the same or different radial positions as the first set of expandable legs.

Figure 1B:
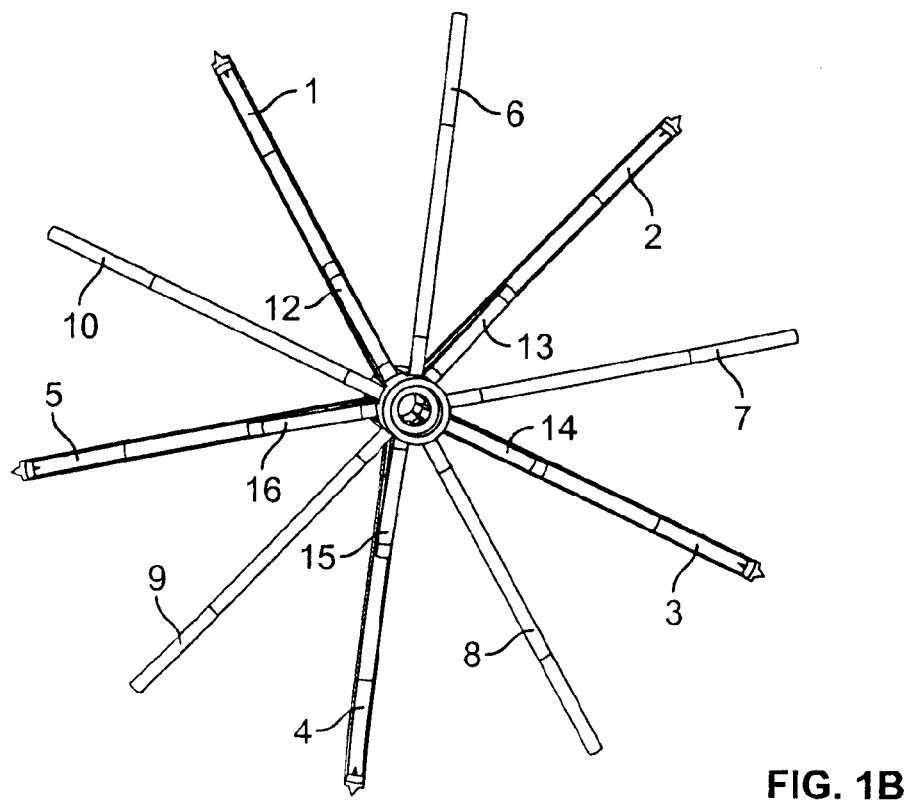
FIG. 1b shows a perspective view of the filter as it would appear looking from 19 to 18.
Figure 1C:
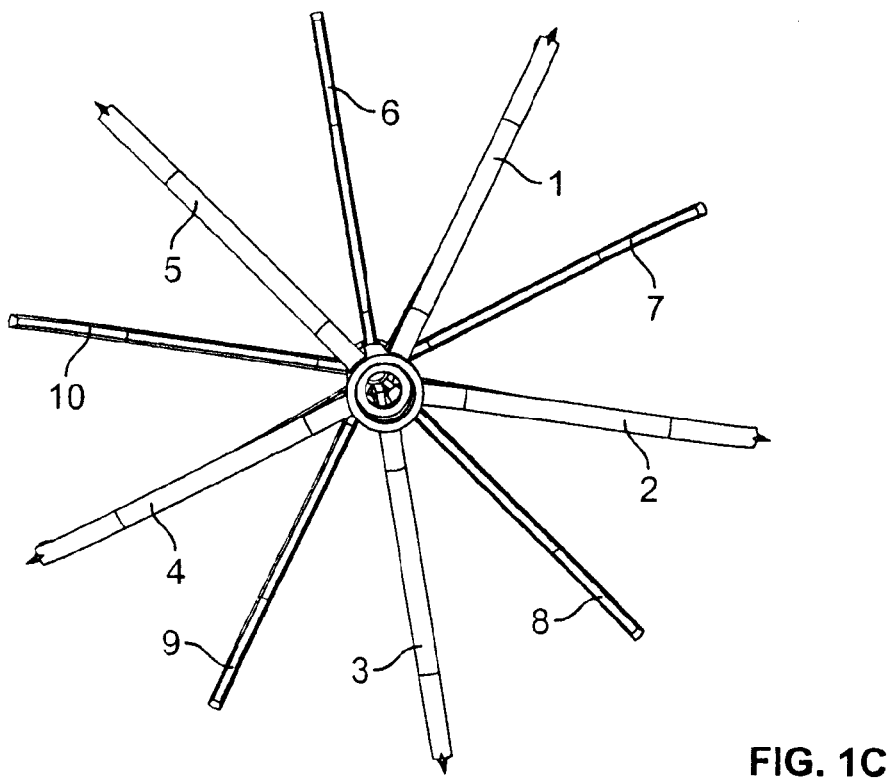
FIG. 1c shows a perspective view of the filter as it would appear looking from 18 to 19.

One embodiment of the assembled filter of the present invention is shown in FIGS. 1*a*, *b*, *c*. The filter is formed from two sets of five expandable legs, the first expandable set, 1, 2, 3, 4, 5 and the second expandable set, 6, 7, 8, 9, 10. These expandable legs form a cage 11. The cage 11 may take the shape of a ball or sphere when deployed. The filter comprises a first set of expandable legs, 1, 2, 3, 4, 5, a second set of expandable legs 6, 7, 8, 9, 10, and a third set of expandable legs 12, 13, 14, 15, 16. The expandable segment of each leg in the third set may form a curvilinear shape when deployed. The first set of expandable legs are attached or secured to the first tube 17, with proximal 18 and distal 19 ends, relative to the placement of the first set of expandable legs. As is apparent from FIG. 1*b*, the second set of expandable legs, 6, 7, 8, 9 and 10 are positioned at different radial points along the circumference of the first tube 17 as compared with the first set of expandable legs, 1, 2, 3, 4 and 5. In this embodiment, the third set of expandable legs, 12, 13, 14, 15 and 16, are positioned at the same radial points along the circumference of the first tube 17 as the first set of expandable legs, 1, 2, 3, 4, 5 and 6.

The filter comprises at least two tubes, a first tube, a second tube and a third tube that are inserted into each other to form the filter. In some embodiments, the third tube forms part of the second tube, i.e., the third tube and the second tube may be cut or formed from a single tube. In order to permit the third tube and the second tube to be inserted into the first tube, the external diameters of the second and third tubes are smaller than the internal diameter of the first tube.

Figure 2A:
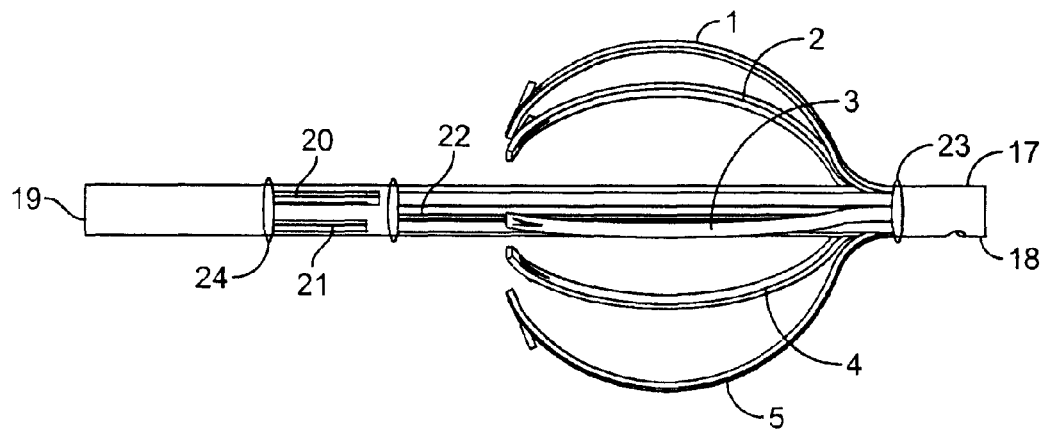
FIG. 2a shows a side view of the first tube.
Figure 2B:
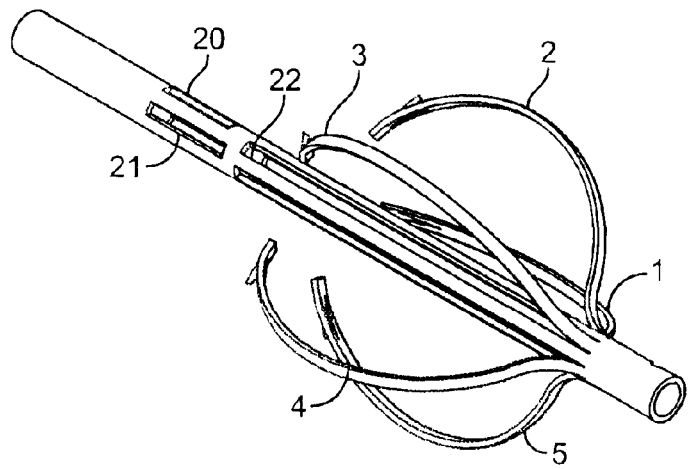
FIG. 2b shows a second perspective of the first tube.
Figure 2C:
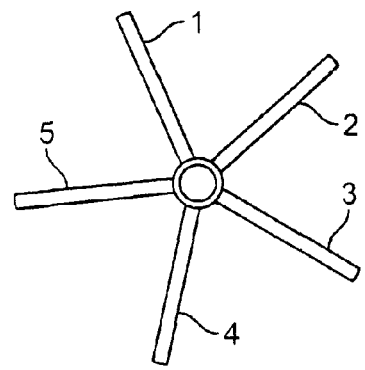
FIG. 2c shows a perspective of first tube as it would appear looking from 18 to 19.

FIGS. 2a, b and c show various perspective views of the first tube. The first tube 17 contains a plurality of a first set of slots 22 as a well as plurality of a second 20 and third 21 set of slots which are parallel to the long or cylindrical axis of the first tube. The first set of expandable legs 1, 2, 3, 4 and 5 are attached on the first tube 17 at position 23 which is from about 2 mm to about 10 mm from 18, the proximal end of the first tube. The first set of expandable legs may be secured at about 2 mm to about 8 mm, from about 4 mm to about 7 mm or at about 5 mm from the proximal end 18 of the first tube.

The first tube may have a length of between 25 mm to about 60 mm, from about 30 mm to about 50 mm, from about 30 mm to about 40 mm or about 35 mm. The first set of expandable legs may have a length of about 10 mm to about 30 mm, from about 15 mm to about 25 mm or about 20 mm. Similarly, the first set of slots 22 may have a length of about 10 mm to about 30 mm, from about 15 mm to about 25 mm or about 20 mm. The radial positions of the first set of slots on the first tube corresponds to the radial positions of the first set of expandable legs.

The second and third set of slots are positioned closest to the distal 19 end of the first tube. For example, the second and third set of slots may start at a position from the distal end 19 of the first tube from about 2 mm to about 15 mm, from about 4 mm to about 8 mm or from about 5 mm to about 6 mm. The second set of slots may range in length from about 1 mm to about 10 mm, from about 2 mm to about 8 mm or from about 4 mm to about 6 mm. The third set of slots may range in length from about 2 mm to about 8 mm, from about 3 mm to about 6 mm or from about 3.5 mm to about 4.5 mm. The radial positions of the second and third set of expandable slots corresponds to the radial positions of the second set of expandable legs.

The first set of expandable legs may have a width 25 ranging from 0.05 mm to about 1.5 mm, from about 0.1 mm to about 1.0 mm, from about 0.4 mm to about 0.8 mm or about 0.5 mm. The width of the first set of expandable legs may be constant or vary. For example, in one embodiment, the width of the first set of expandable legs may taper or narrow from the point where it is secured 23 to the barbed end. The expanded diameter of the first set of expandable legs may range from 10 mm to about 20 mm, from about 12 mm to about 18 mm, from about 14 mm to about 16 mm or about 15 mm (26). The internal diameter of the first tube may range from about 1.0 mm to about 1.6 mm, from about 1.2 mm to about 1.6 mm, from about 1.4 mm to about 1.5 mm or about 1.5 mm. The thickness of the first tube may vary from about 0.4 mm to about 0.8 mm, from about 0.5 mm to about 0.7 mm or from about 0.5 mm to about 0.55 mm. The thickness of first tube may be constant or may vary from 18 to 19. The ends of the first tube, 18, 19, may be straight or beveled.

Figure 3A:
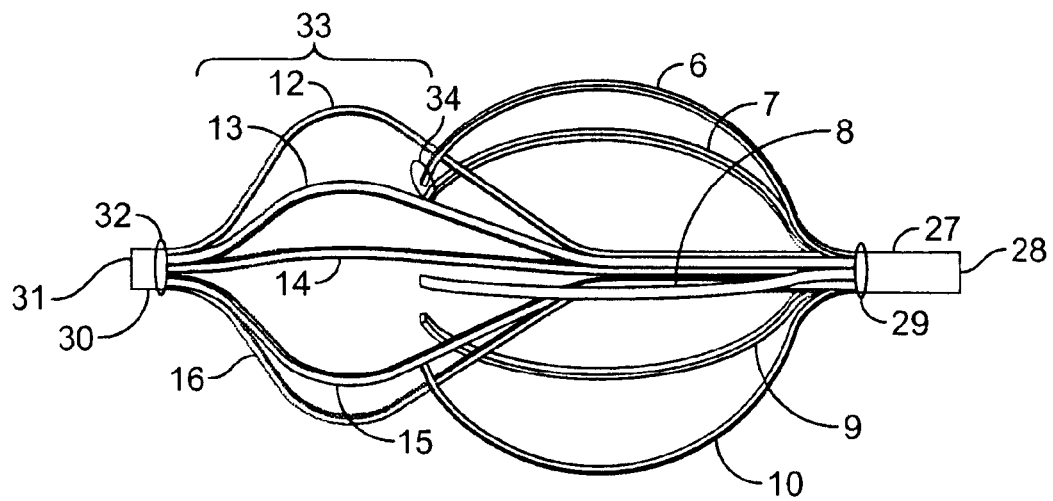
FIG. 3a shows a side view of the second and third tubes.
Figure 3B:
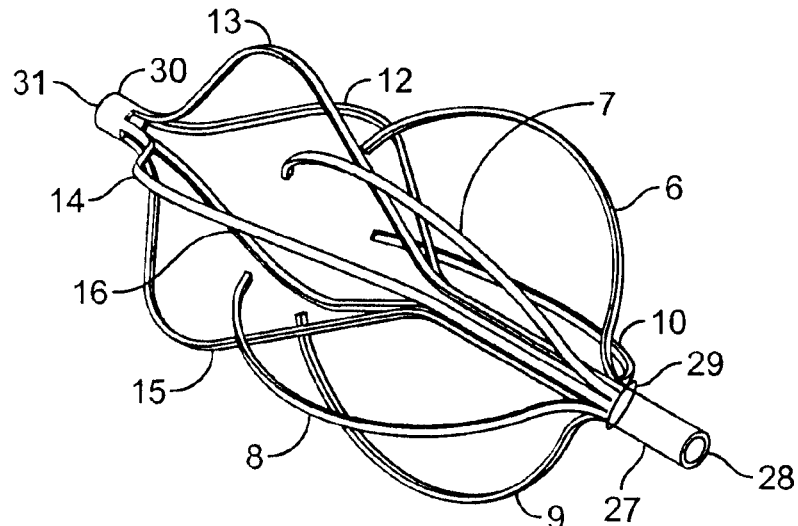
FIG. 3b shows a second perspective of the second and third tubes.
Figure 3C:
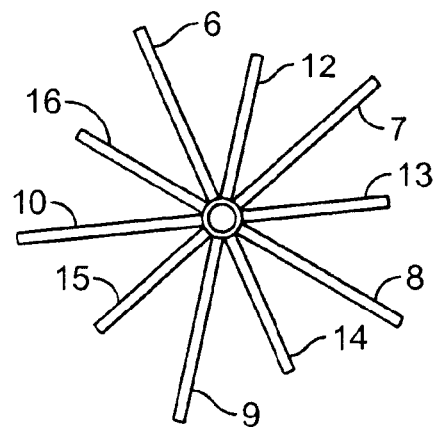
FIG. 3c shows a perspective of second and third tube as it would appear looking from 28 to 31.

FIGS. 3a, b and c show various perspective views of the second and third tubes. The second set of expandable legs are secured at a point 29 where point 29 is closest to the distal end 28 of the second tube 27. The second set of expandable legs, 6, 7, 8, 9 and 10 has a free end 34. The third set of expandable legs 12, 13, 14, 15 and 16 are secured to the third tube 30 at 32. The expandable segments 33 of the third set of expandable legs may vary in length. When assembling the filter, the proximal end of the third tube 31 is inserted into the distal end 19 of the first tube. As is evident from the FIG. 3c which shows a perspective view as it would appear looking from the distal 28 end to the proximal 31 end, the radial positions of the third set of expandable arms 12, 13, 14, 15, and 16 are off-set from the radial positions of the second set of expandable legs 6, 7, 8, 9 and 10. In the embodiment shown, the radial position of the third set of expandable legs bisects the radial degrees between two pairs of the second set of expandable legs. For example, if the second set of expandable legs, 6 and 7 lie at 0° and at 720, respectively, then the radial position of the third set of expandable leg 12 is at about 36°.

The dimensions of the second and third tubes as well as the second and third set of expandable legs may vary. For example, the straight length of the second and third tubes may range from about 15 mm to about 50 mm, from about 20 mm to about 35 mm or from about 25 mm to about 30 mm. The length of the second set of expandable legs, 6, 7, 8, 9 and 10 may be identical to the length of the first set of expandable legs. The thickness or width of the second set of expandable legs may range from about 0.05 mm to about 1.5 mm, from about 0.1 mm to about 1.0 mm, from about 0.4 mm to about 0.8 mm and about 0.4 mm. The thickness or width along the length of the leg may be constant or taper from the end where the second set of expandable legs is secured 29 to the free end 34. The expanded diameter of the second set of expandable legs may range from 10 mm to about 20 mm, from about 12 mm to about 18 mm, from about 14 mm to about 16 mm and about 15 mm. The second tube or the third tube may comprise a solid cylinder and may be cut from a single tube, where the third tube may form part of the second tube. The thickness of the second and the third tube may range from about 0.3 mm to about 0.6 mm, from about 0.4 mm to about 0.5 mm or from about 0.4 mm to about 0.45 mm.

The external diameter of the second and third tubes may vary from about 0.5 mm to about 1.5 mm, from about 0.8 mm to about 1.5 mm, from about 1.2 mm to about 1.5 mm, from 1.4 mm to about 1.5 mm or about 1.45 mm, provided that the external diameter of the second and third tubes are each less than the internal diameter of the first tube. The external diameters of the second and third tube may be the same or different. The thickness of first tube may be constant or may vary from 28 to 31. The ends of the first tube, 28, 31, may be straight or beveled.

Figure 4A:
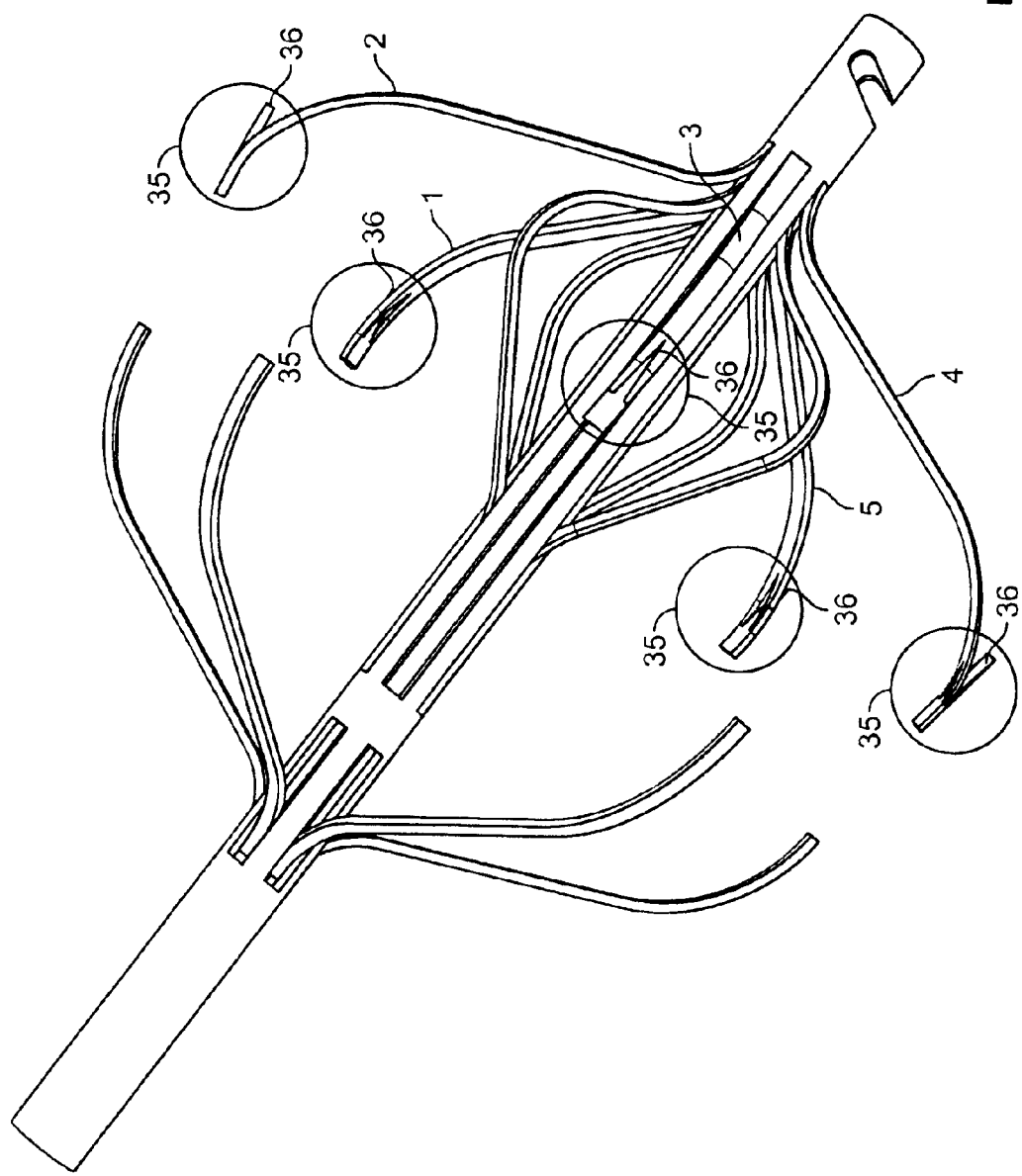
FIG. 4a shows a close-up illustration of the first set of expandable legs with the barbs.
Figure 4B:
FIG. 4b shows various embodiments of the barb design.
Figure 4B:
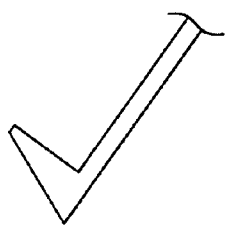
Figure 4B:
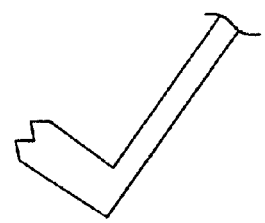
Figure 4B:
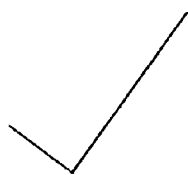
Figure 4B:
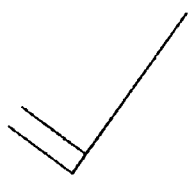
Figure 4B:
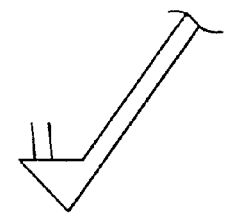

Each of the free ends 35 of the first set of expandable legs 1, 2, 3, 4, 5 may have a barb 36 (FIG. 4a). The barbs may assume various designs and angles. For example, the angle between the barb and the free end of the leg where the barb is attached to may range from about 10 degrees to about 200 degrees, from about 40 degrees to about 200 degrees, from about 60 degrees to about 190 degrees, from about 90 degrees to about 180 degrees or from about 95 to about 105 degrees relative to a straight line set when the first set of expandable legs is in an undeployed position. The barbs can be any desired shape or configuration, the examples of which are shown in FIG. 4b. In one embodiment, the barb has a convex shape allowing it to bend on itself when the filter is deployed. The shape, configuration, dimension, angle and penetration depth of the barbs may vary between legs and may be present on some or all of the first, second and third expandable sets of legs. In one embodiment, the angle of the barbs is set such that the barbs will not penetrate into the vessel wall until the internal vessel dimension of at least about 18 mm has been encountered by the filter. It will be appreciated that one of ordinary skill in the art could select both the shape of the barb and the angle by routine experimentation and that the shape of the cage 11 formed by the first and second set of expandable legs can be constrained to meet this requirement.

Figure 5A:
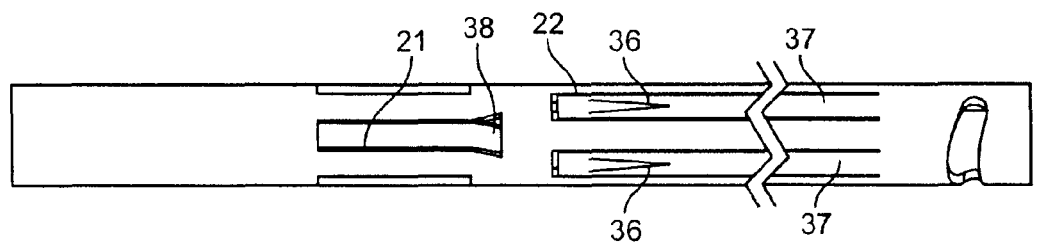
FIG. 5a shows a cross section of a slot with a flared portion.
Figure 5B:
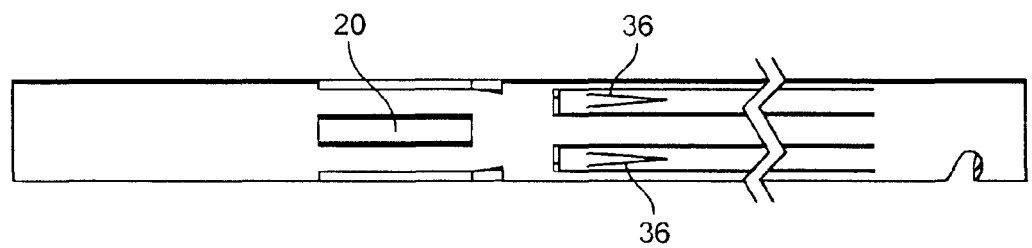
FIG. 5b shows a cross section of a slot with a straight or unflared shape.
Figure 5C:
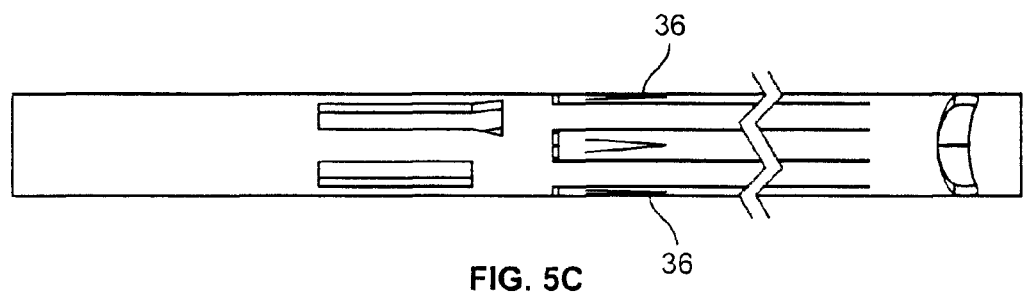
FIG. 5c shows cross section of unflared and flared slots.

The first set of slots 22 are designed to permit the third set of expandable legs to deploy through the openings 37 (FIG. 5a). There may be two sets of additional slots, 20 and 21 positioned radially on the first tube 17 (FIGS. 5a and b). In some embodiments, the third set of slots 21 may have a flare 38 at one end. The shape of the flared end 38 may vary, but is preferably trapezoidal. The third set of slots 21 permit the second set of expandable legs to deploy. The range of width of these set of slots corresponds to the width second set of expandable legs. The length of the slots ranges from about 2 mm to about 10 mm, from about 4 mm to about 6 mm or about 5 mm. The length of the flared portion ranges from about 0.05 mm to about 2 mm, from about 0.5 mm to about 1.5 mm, from about 0.75 mm to about 1.25 mm or about 1 mm.

The second set of slots 20 may not contain a flared portion. The width of the second set of slots 20 corresponds to the width of the second set of expandable legs. The length of the unflared slot ranges from about 1 mm to about 6 mm, from about 2 mm to about 4 mm or about 4 mm.

Figure 6A:
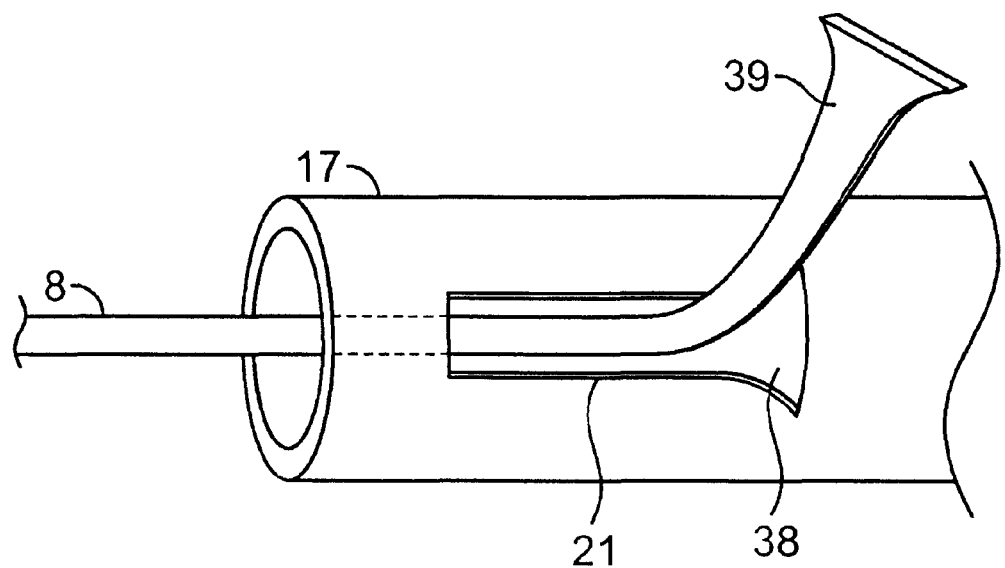
FIG. 6a shows deployment of the second set of expandable legs through a flared slot.
Figure 6B:
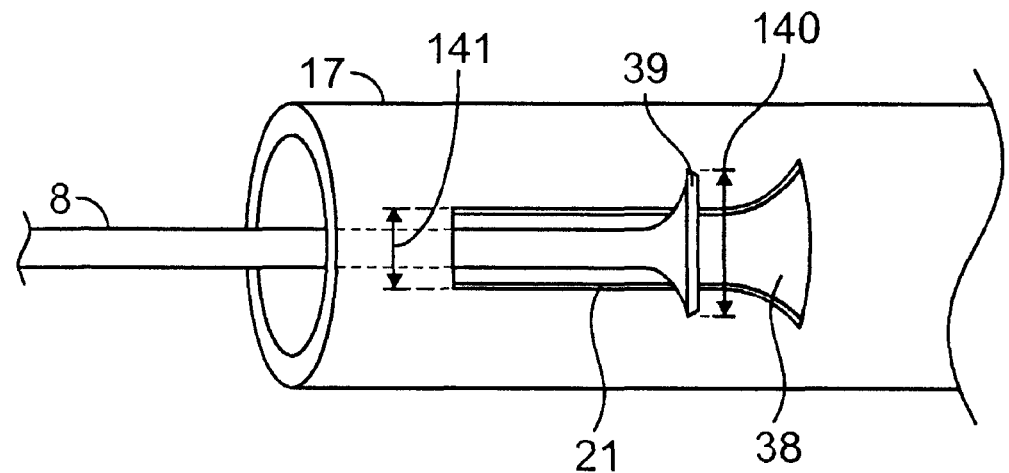
FIG. 6b illustrates how the flared strut configuration prevents disassembly.

In some embodiments, only a limited number of second and third slots contain flared portions. The radial position on the circumference of the first tube 17 corresponds to the radial position of the second set of expandable legs. For example, in one embodiment, the radial position of the second set of expandable legs is about 108° for F, about 180° for G, about 252° for H, about 324° for 1 and about 36° for J. The second and third set of slots would be positioned at about 108°, about 180°, about 252°, about 324° and about 360°, corresponding with the second set of expandable legs. In this embodiment, the number of flared slots 21 ranges from 0-5, 1-5, 2-4 or 2-3. If a flared slot 21 is present, then the second set of expandable legs which correspond to the slot having the flared portion 38 are also flared. FIG. 6a illustrates deployment of one expandable leg, 8, where there is flaring at the end of the expandable leg 39. FIG. 6b illustrates how the flare 39 can prevent disassembly of the filter because the width of the flared portion 39, 140, is greater than the width 141 of the unflared portion of the slot.

The filter of the present invention is assembled from the first, second and third tubes. The third tube 30 is inserted into the end 19 of the first tube. The third set of expandable legs, 12, 13, 14, 15 and 16 and the second set of expandable legs 6, 7, 8, 9 and 10 are straight, i.e., not expanded during insertion. The free ends 34 of the second set of the expandable legs are inserted into the second and third sets of slots and the third set of expandable legs are positioned in the first set of slots.

Figure 7:
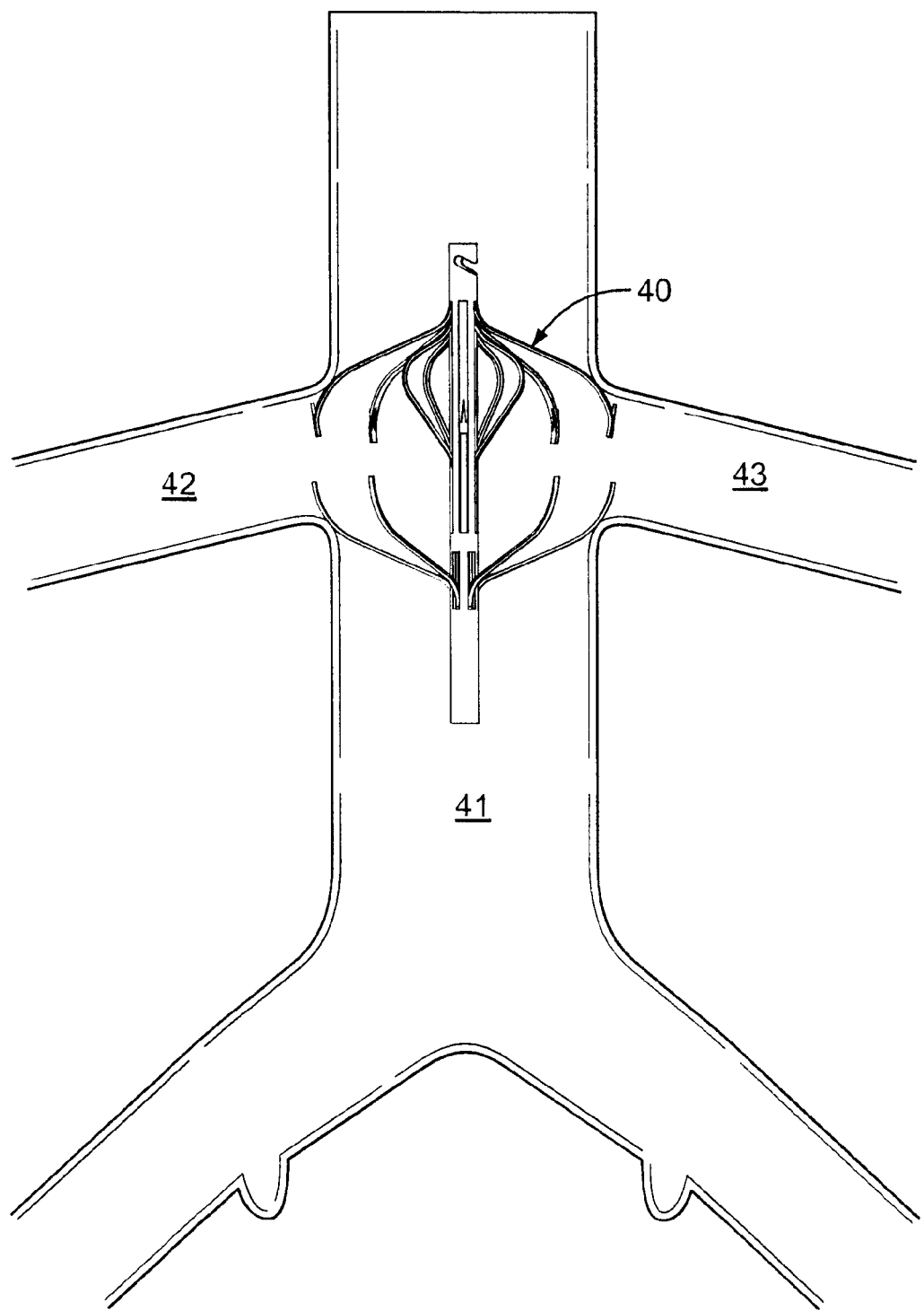
FIG. 7 shows deployment of the filter in the inferior vena cava.
Figure 8:
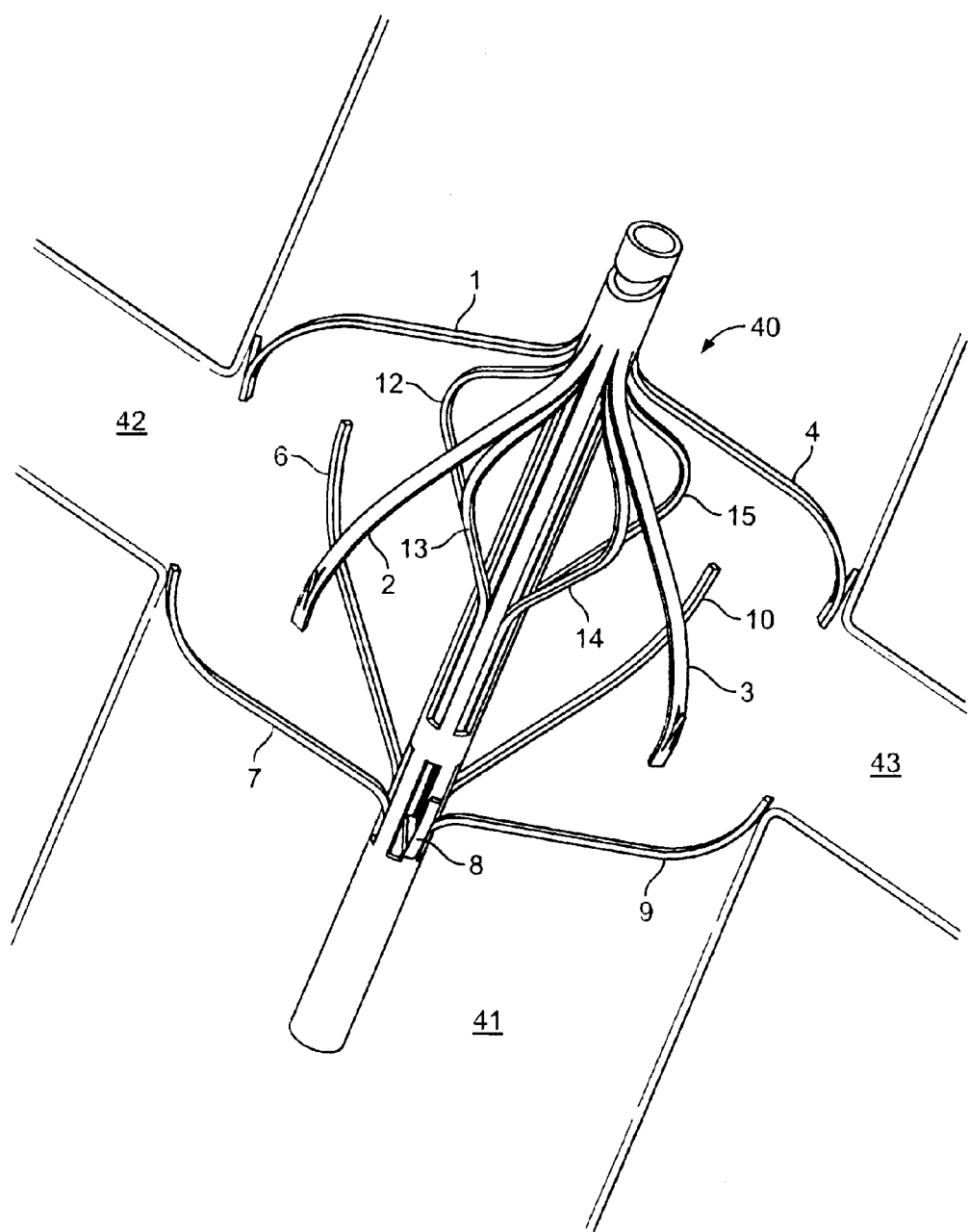
FIG. 8 shows the deployed filter.

The filter of the present invention may be deployed by any desired delivery system. FIG. 7 shows the filter 40 which is deployed in the inferior vena cava 41 at or below the junction of the right 42 and left 43 renal veins. The diameter of the axially collapsed filter may range from about 0.8 mm to about 5.5 mm, from about 1.2 mm to about 4.5 mm, or from about 1.5 mm to about 3 mm, with one specific embodiment of about 2 mm. The diameter of the delivery system, such as a delivery catheter, may range from about 0.8 mm to about 5.5 mm, from about 1.2 mm to about 4.5 mm, or from about 1.8 to about 3 mm. In one embodiment, the collapsed filter is encased in a delivery catheter of about 6 French (2 mm) in diameter. In another embodiment, the filter is delivered by a delivery catheter of about 8 French (2.67 mm) in diameter. The filter may be deployed by a simple pin and pull delivery (see Cordis TrapEase Permanent Vena Cava Filter with the VisEase Angiographic Vessel Dilator [on-line]. Retrieved on Aug. 1, 2008, from URL: <http://www.mitek.com/home.jg/ml?loc=USENG & page=viewContent&contentId=09008b9880ffdcbf& nodekey=/Prod_Info/Type/Endovas cular_Disease_Management/ Vena_Cava_Filters&parentId=fc0de00100001215>. The filter may be placed in a vessel such as the inferior vena cava using ultrasound at a patient's bedside or under standard fluoroscopy. A catheter containing the undeployed filter is inserted and the filter extruded from the catheter. The filter than then floats into place at the junction of the left and right renal vein. After insertion and deployment, the filter assumes a position within the inferior vena cava at or near the junction of the left and right renal veins 42, 43 (FIG. 8). The first and second sets of expandable legs 1, 2, 3, 4, 5 and 6, 7, 8, 9, 10 form two hemispheres respectively in the vessel creating a cage or sphere 11. The barbs of the filter open and insert into the vessel wall when the width of the vessel wall exceeds the diameter of the filter. The barbs are on the ends of the legs which are on the outer curvature of the spheres. The sphere shape prevents barb deployment until the diameter of the blood vessel exceeds the deployment diameter for the barbs. The deployment diameter for the barbs may range from about 7 mm to about 20 mm, from about 10 mm to about 18 mm or about 15 mm.

Figure 9:
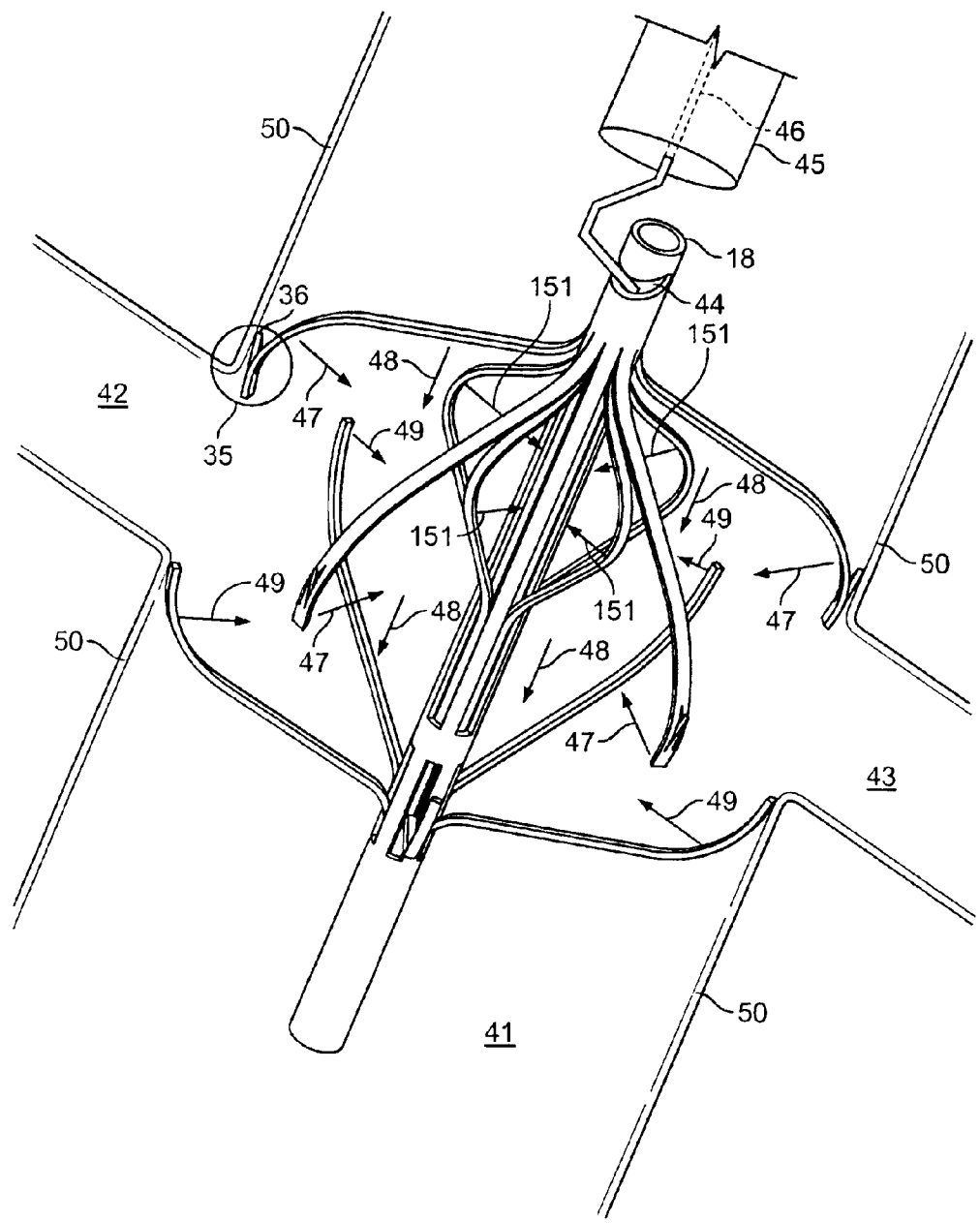
FIG. 9 shows retrieval of the filter.

The invention provides for a method for retrieving the vena cava filter. FIG. 9 illustrate retrieval of one embodiment of the filter. A catheter 45, the internal dimension of which is greater than the external dimension of the first tube 17, is inserted into a vessel such as the jugular vein and moved to where the filter is positioned on the vessel wall. A snare 46 is pushed through the catheter until the snare grabs the notch 44. A notch structure is present on the first tube 17. The notch 44 is shown in this embodiment as a semicircular structure. The notch may have a variety of different structures such as a rectangular hole or a square hole as long as it permits efficient hooking of the filter 40 by a snare 46. The notch 44 may be positioned from about 2 mm to about 10 mm from the end 18, from about 4 mm to about 8 mm, from about 6 mm to about 8 mm and about 5 mm. The physician exerts tension on the filter 40 by pulling back on the snare 46. The tension exerted may be in the range of about 0.45 kilogram (kg) to about 4.5 kg, but the appropriate amount of tension may be determined by one of ordinary skill in the art based on clinical experience in the art. Various embodiments of the notch 44 are shown in FIG. 10 ((a)-(e)). The notch 44 may assume many different shapes such as a hook (a), a L shape (b), a T-shape (c), a reverse C-shape (d) and a semi-circular shape (e) as long as it permits secure capture by the snare 46. The snare may also take many different forms, such as a loop or a wire basket. The snare may be formed from several interconnected pieces of material or from a single piece of material. In addition, the snare may comprise a locking mechanism that locks once the snare grabs the notch on the filter. The catheter 45 is pushed over the snare and each leg of the first set of expandable legs 1, 2, 3, 4, 5 until each expandable leg retracts from the wall 50 of vena cava. The barbs 36 dislodge from the vessel wall and move inwards 47. As each leg of the first set 1, 2, 3, 4, 5 of expandable legs retracts from the vessel wall, the expandable segments 33 of the third set of expandable legs 12, 13, 14, 15, 16 straighten and push downwards 51 away from the snare 46. The vector of force 48 pushes the second tube 17 away from the snare 46 creating a vector of force 49 which pushes the second set of expandable legs 6, 7, 8, 9, 10 away from the vessel wall 50. The catheter 45, which encompasses the retracted filter, is then withdrawn from the vessel.

Figure 11:
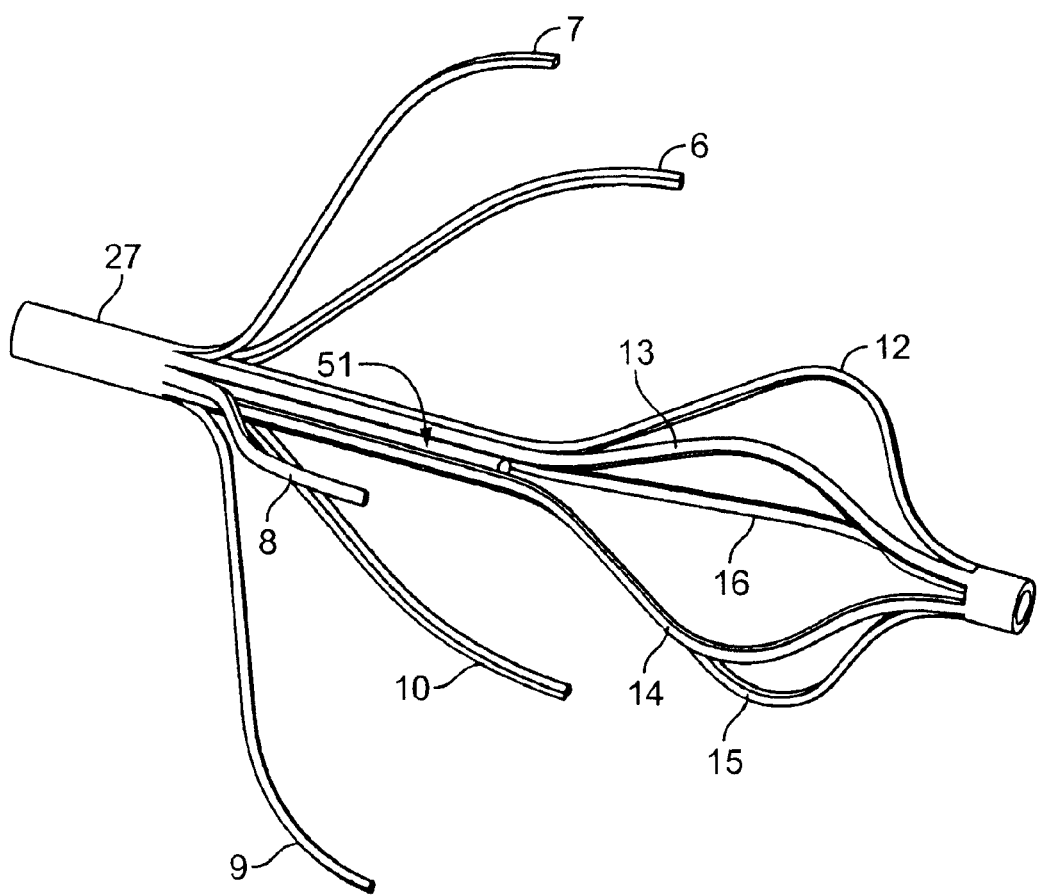
FIG. 11 illustrates one embodiment of the second tube where the second set of expandable arms are welded to a fourth tube or pin.

In order to facilitate transmittal of the force vector 48, a solid pin or hollow tube 51 is inserted in the second tube 27 and laser welded to the legs of the third set of expandable legs 12, 13, 14, 15, 16 (FIG. 11). When the third set of expandable legs 12, 13, 14, 15, 16 are pushed away 48 from the snare 46, the pin or tube 51 transmits the vector of force 49 equally across all of the second set of expandable legs 6, 7, 8, 9, 10. The tube or pin 51 also facilitates simultaneous deployment of the third set of expandable legs 12, 13, 14, 15 and 16. The length of the pin or tube welded to the third set of expandable legs may range from about 2 mm to about 8 mm, from about 3 mm to about 6 mm, or about 4 mm. The pin or tube may be solid or hollow.

Figure 12A:
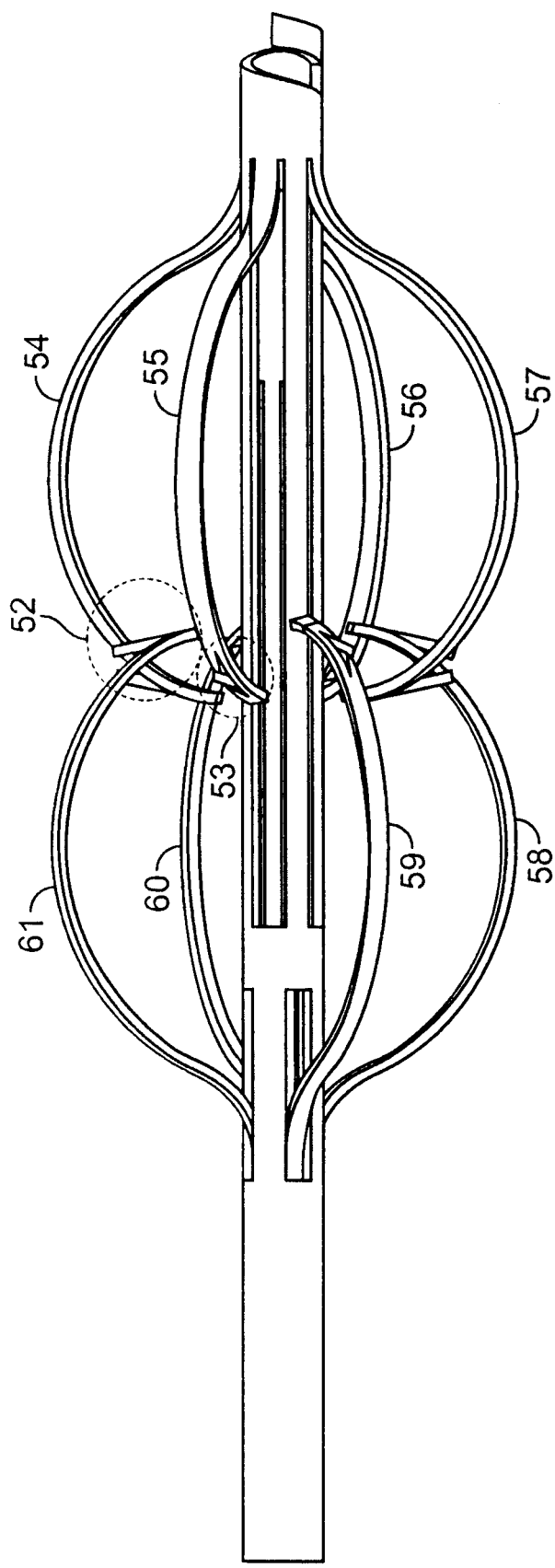
FIGS. 12a, 12b and 12c show various embodiments of the filter.
Figure 12B:
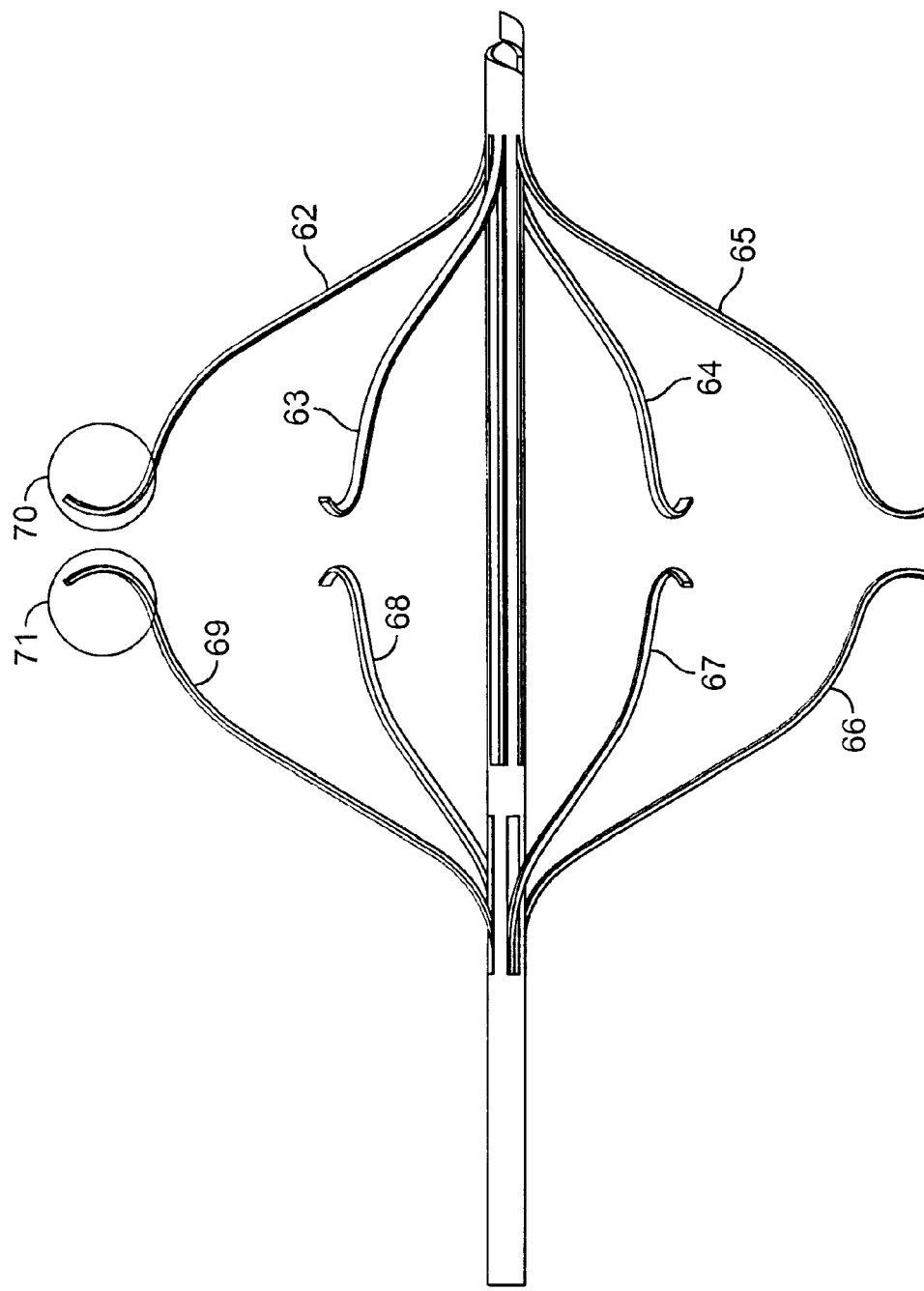
Figure 12C:
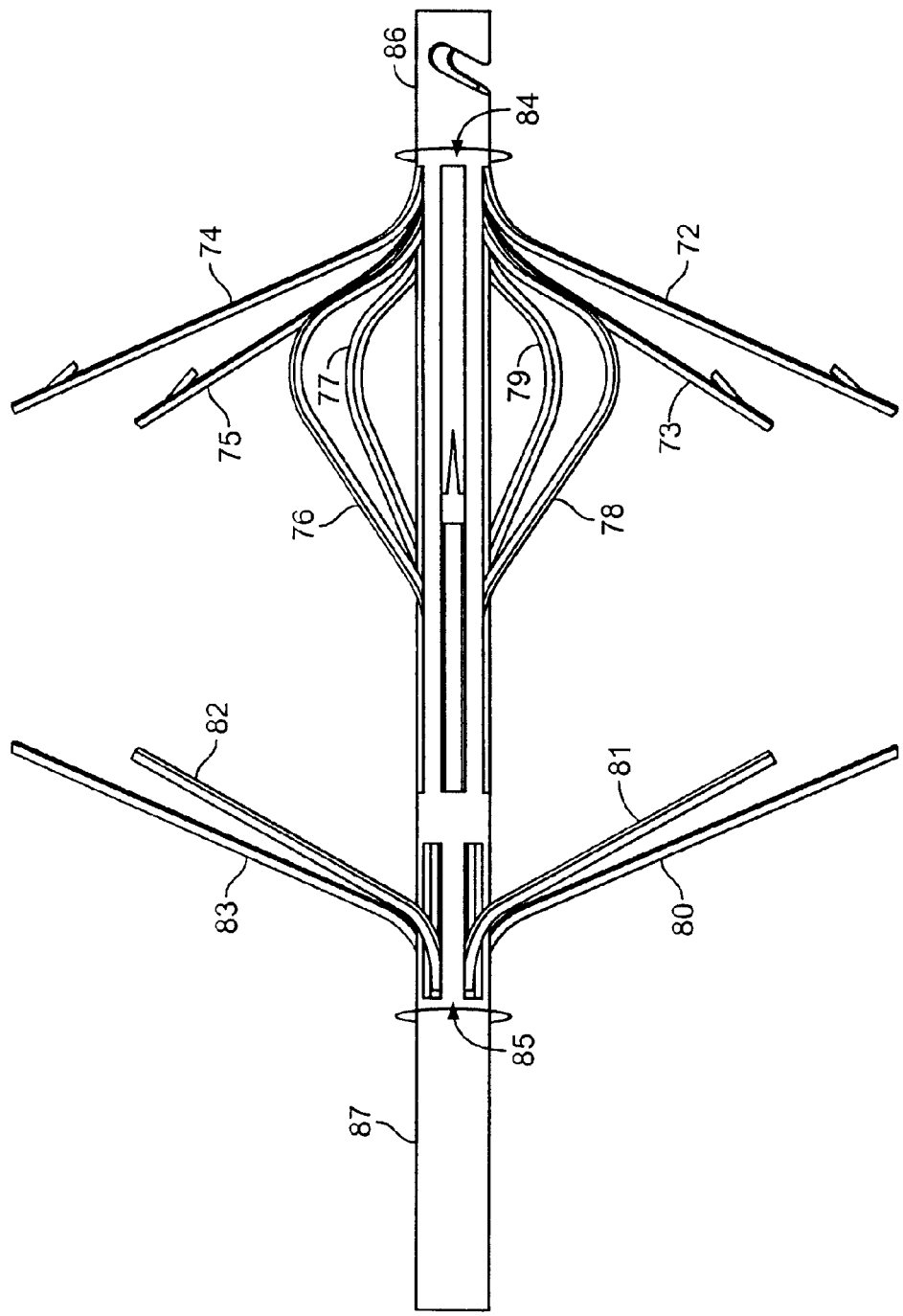

Various embodiments of the filter are encompassed by the invention. In FIG. 12a, the filter is comprised of two sets of expandable legs 54, 55, 56 and 57 and 58, 59, 60 and 61, both of which have barbs 52 and 53 on the free ends. FIG. 12b shows an embodiment of the filter where the free ends 70, 71 of the expandable legs, 62, 63, 64 and 65 and 66, 67, 68 and 69 are curvilinear. FIG. 12c shows an embodiment of the filter where the expandable legs 72, 73, 74 and 75 and 80, 81, 82 and 83 are straight. The third set of expandable legs are shown as 76, 77, 78 and 79, the first set of expandable legs are attached at 84, the second set of expandable legs are attached at 85, the first tube is 86 and second tube is 87.

The filter may be made of laser cut, self-expanding nitinol. The filter may also be made of any metal, such as titanium, platinum, gold, a metal alloy, such as stainless steel, or a memory metal. In one embodiment, each of the expandable legs of the first and second sets comprise memory metal. In another embodiment, the expandable segment of the expandable legs of the third set comprises memory metal. The filter may further be made of any biocompatible material that is durable and non-corrosive. Examples of biocompatible material include a synthetic material such as polyurethanes, segmented polyurethane-urea/heparin, poly-L-lactic acid, cellulose ester, polyethylene glycol, polyvinyl acetate, dextran and gelatin, a naturally-occurring material such as basement membrane components such as collagen, elastin, laminin, fibronectin, vitronectin; fibrin, cellulose, and amorphous carbon, or fullerenes. In some embodiments of the invention, the filter is made of biodegradable, bioabsorbable, bioerodable material and/or a mixture thereof. Examples of bioabsorbable material include copolymers of glycolide with lactide or 8-caprolactone, and poly(p-dixanone). The filter may be made of a single material or different materials. U.S. Patent Publication No. 20070191932. U.S. Pat. No. 7,147,649.

The filter of the present invention may be manufactured in numerous ways. The filter may be formed from a single piece of material by removing various portions of a tube or pipe's wall to form the configurations described herein. The filter may also be manufactured by connecting various segments together. Material from the tube wall may be removed using various techniques including laser (e.g. YAG laser), electrical discharge machining, mechanical machining, chemical etching (e.g. photo-fabrication), metal cutting, a combination thereof, or other well known techniques. See U.S. Pat. Nos. 7,329,277, 5,879,381, and 6,117,165.

While the vena cava filters are preferred embodiments of the present invention, filters within the scope of the invention may be placed in any desired blood vessel or endovascular structure. The filter may be placed via a femoral access point, jugular access point or any desired intravascular route. The filter may be placed in the body of the patient permanently or temporarily before being retrieved.

After the vena cava filter is deployed, the vascular endothelial cells or other tissues grow where the filter and vessel wall contact. When the filter is retrieved later, severe damage may occur resulting in laceration or rupture of the vena cava, or at the very least, a focal disruption of the endothelial lining which may predispose to caval stenosis, thrombosis or occlusion. To reduce the risk of complications, the free ends of the legs, other parts of the filter, or the entire filter can be coated with an antiproliferative agent to prohibit the tissue ingrowth, an anti-inflammatory agent or any desired bioactive material. Examples of the antiproliferative agent include paclitaxel. Examples of the anti-inflammatory agent include dexamethasone, corticosterone and prednisolone. Examples of bioactive material that prevent or reduce thrombus formation include anticoagulants, antiplatelets and fibrinolytics.

Any part of the filter or the entire filter can be coated with any desired pharmaceutically active agents. An excipient may be coated on the filter together with the pharmaceutically active agent. The examples of the excipient include binder, matrix, carrier, polymer, hydrogel and nanoparticle. The coating on the filter may be smooth, semi-porous or porous. The coating may be one layer or multiple layers. A pharmaceutically active agent or excipient may also be deposited in a defined structure of the filter, such as tubes, grooves, wells, bells, baskets, etc. A pharmaceutically active agent may also be incorporated into a biocompatible polymer matrix. Polymer matrices include polymers such as poly(lactide-co-glycolide); poly-DL-lactide, poly-L-lactide, and/or mixtures thereof and can be of various inherent viscosities and molecular weights. In one embodiment, poly(DL lactide-co-glycolide) (DLPLG, Birmingham Polymers Inc.) can be used. U.S. Patent Publication No. 20070141107. The pharmaceutically active agent may be released in a sustained, delayed, spiked, controlled or any desired manner.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

The invention claimed is:

1. A filter component having a first end, a second end, and a longitudinal axis extending between the first and second ends, the filter component comprising:

a first set of radially expanding legs, each leg of the first set of legs coupled to and extending continuously away from the first end of the filter component along a longitudinal direction toward the second end of the filter component, wherein each leg of the first set of legs is coupled to the second end of the filter component, and each leg of the first set of legs comprising an intermediate portion defined as the portion of each leg of the first set of legs with the greatest radial displacement from the longitudinal axis and wherein segments of each leg of the first set of legs located on both sides of the intermediate portion of each leg of the first set of legs extend from the intermediate portion of each leg of the first set of legs toward the longitudinal axis; and a second set of radially expanding legs, each leg of the second set of legs coupled to the second end of the filter component, and each leg of the second set of legs comprising an intermediate portion defined as the portion of each leg of the second set of legs with the greatest radial displacement from the longitudinal axis and wherein segments of each leg of the second set of legs located on both sides of the intermediate portion of each leg of the second set of legs extend from the intermediate portion of each leg of the second set of legs toward the longitudinal axis;

wherein the intermediate portions of the first set of legs are displaced a distance along the longitudinal axis of the filter component from the intermediate portions of the second set of legs and wherein the first end of the filter component defines a proximal-most portion of the filter component and the second end of the filter component defines a distal-most portion of the filter component.

2. The filter component of claim 1, further comprising:

a first end portion of the filter component coupled to one or more legs adjacent the first end of the filter component, and a second end portion of the filter component coupled to one or more legs adjacent the second end of the filter component.

3. The filter component of claim 2, wherein the first end portion and the second end portion are generally tubular in shape.

4. The filter component of claim 3, wherein the tubular first end portion is substantially coaxially aligned with the tubular second end portion.

5. The filter component of claim 2, wherein each leg of the first set of legs comprises:

a first end coupled to the first end portion of the filter component;

a first segment disposed between the first end of the leg and the intermediate portion of the leg;

a second end coupled to the second end portion of the filter component;

and a second segment disposed between the second end of the leg and the intermediate portion of the leg.

6. The filter component of claim 5, wherein each leg of the first set of legs is disposed along a smooth curve.

7. The filter component of claim 5, wherein the second segment of each leg of the first set of legs further comprises a radially expanding portion and a portion disposed substantially parallel to the longitudinal axis of the filter component.

8. The filter component of claim 1, wherein the filter component is integrally formed from a single piece of material.

9. The filter component of claim 8, wherein the filter component comprises a shape memory alloy.

10. The filter component of claim 1, wherein one or more barbs are coupled to one or more legs of the filter.

11. A filter having a first end, a second end, and a longitudinal axis extending between the first and second ends, the filter comprising:

a first end portion;

a second end portion;

a first set of radially expanding legs, each leg of the first set of legs coupled to and extending continuously away from the first end portion of the filter along a longitudinal direction toward the second end portion of the filter, and each leg of the first set of legs comprising a first end coupled to the first end portion and a second end coupled to the second end portion, and each leg of the first set of legs having an intermediate portion defined as the portion of each leg of the first set of legs with the greatest radial displacement from the longitudinal axis and wherein segments of each leg of the first set of legs located on both sides of the intermediate portion of each leg of the first set of legs extend from the intermediate portion of each leg of the first set of legs toward the longitudinal axis; and a second set of radially expanding legs, each leg of the second set of legs coupled to the second end portion of the filter, and each leg of the second set of legs comprising a first end and a second end, the second end coupled to the second end portion, and each leg of the second set of legs having an intermediate portion defined as the portion of each leg of the second set of legs with the greatest radial displacement from the longitudinal axis and wherein segments of each leg of the second set of legs located on both sides of the intermediate portion of each leg of the second set of legs extend from the intermediate portion of each leg of the second set of legs toward the longitudinal axis, wherein the first end portion of the filter defines a proximal-most portion of a filter component and the second end portion of the filter defines a distal-most portion of the filter component, the filter component being integrally formed from a single piece of material, and wherein the intermediate portions of the first set of legs are displaced a distance along the longitudinal axis of the filter from the intermediate portions of the second set of legs.

12. The filter of claim 11, wherein the first set of legs extends from the first end portion toward the second end portion and the second set of legs extends from the second end portion toward the first end portion.

13. The filter of claim 11, wherein the the first set of legs defines a first filter basket and the second set of legs defines a second filter basket displaced a distance along the longitudinal axis of the filter from the first filter basket.

14. The filter of claim 11, wherein the first and second end portions are generally tubular in shape.

15. The filter of claim 14, further comprising an outer tube having a first end, a second end, and longitudinally aligned slots disposed between the first and second ends, wherein the first and second end portions are configured to be disposed within the outer tube and wherein the first and second sets of legs are configured to extend through the slots.

16. The filter of claim 11, wherein each leg of the first and second sets of legs comprise a generally smooth curve.

17. The filter of claim 11, wherein a segment of each leg of the first set of legs is disposed substantially parallel to the longitudinal axis of the filter.

18. The filter of claim 11, wherein one or more barbs are coupled to one or more legs of the filter.

19. The filter of claim 18, wherein the barbs are integrally formed with the legs.

20. The filter of claim 11, wherein the filter comprises a shape memory alloy.

* * * * *